(12) United States Patent
Ehrnsperger et al.

(10) Patent No.: US 6,579,457 B1
(45) Date of Patent: Jun. 17, 2003

(54) LIQUID TRANSPORT MEMBER FOR HIGH FLUX RATES BETWEEN A PORT REGION AND AN OPENING

(75) Inventors: Bruno Johannes Ehrnsperger, Frankfurt (DE); Mattias Schmidt, Idstein (DE); Karl Michael Schumann, Cincinnati, OH (US); Fred Naval Desai, Fairfield, OH (US); Gary Dean Lavon, Oberursel (DE); Gerald Alfred Young, Cincinnati, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/720,169

(22) PCT Filed: Jun. 29, 1999

(86) PCT No.: PCT/US99/14634
§ 371 (c)(1),
(2), (4) Date: Dec. 20, 2000

(87) PCT Pub. No.: WO00/00701
PCT Pub. Date: Jan. 6, 2000

(51) Int. Cl.$^7$ ................................................ B01D 63/00
(52) U.S. Cl. ........................ 210/321.6; 96/6; 96/155; 137/140; 210/258; 210/321.84; 210/321.87; 210/460; 210/500.1
(58) Field of Search ................................ 210/96.2, 137, 210/153, 170, 242.4, 257.1, 257.2, 258, 263, 321.6, 321.65, 416.1, 459, 484, 497.01, 500.1, 500.23, 503, 505, 510.1, 637, 643, 644, 649, 650, 767, 924; 137/123, 140, 142, 145, 147

(56) References Cited

U.S. PATENT DOCUMENTS

| | | | |
|---|---|---|---|
| 2,734,015 A | * | 2/1956 | Wettstein et al. ...... 210/321.87 |
| 4,126,556 A | * | 11/1978 | Swanson et al. ......... 210/242.4 |
| 4,735,722 A | * | 4/1988 | Krepak .................. 210/500.23 |
| 4,820,293 A | | 4/1989 | Kamme ...................... 604/368 |
| 5,006,264 A | * | 4/1991 | Acuna ........................ 210/767 |
| 5,082,723 A | | 1/1992 | Gross et al. |
| 5,108,383 A | | 4/1992 | White ......................... 604/368 |
| 5,186,831 A | * | 2/1993 | DePetris ................. 210/242.4 |
| 5,385,672 A | * | 1/1995 | Peterson et al. ............ 210/637 |
| 5,387,207 A | | 2/1995 | Dyer et al. ................. 604/369 |
| 5,563,179 A | | 10/1996 | Stone et al. .................. 521/64 |
| 5,728,292 A | | 3/1998 | Hashimoto et al. ......... 210/136 |
| 5,733,581 A | | 3/1998 | Barboza et al. ............ 425/72.2 |
| 5,770,086 A | * | 6/1998 | Indriksons et al. ......... 210/643 |
| 5,833,927 A | * | 11/1998 | Raybuck et al. ............ 210/460 |

FOREIGN PATENT DOCUMENTS

| | | |
|---|---|---|
| EP | 0 365 565 B1 | 5/1990 |
| EP | 0 439 890 A1 | 8/1991 |
| EP | 0 773 058 A1 | 5/1997 |
| EP | 0 780 148 A1 | 6/1997 |
| EP | 0 810 078 A1 | 12/1997 |
| FR | 2746255 * | 9/1997 |
| WO | WO 97/35656 | 10/1997 |
| WO | WO 97/47375 | 12/1997 |
| WO | WO 00/00701 * | 1/2000 |

* cited by examiner

*Primary Examiner*—Joseph Drodge
(74) *Attorney, Agent, or Firm*—Eileen L. Hurghett; Edward J. Milbrada; Caroline Wei-Berk

(57) ABSTRACT

The present invention is a liquid transport member with significantly improved liquid handling capability, which has at least one bulk region and a wall region that completely circumscribes said bulk region, and which comprises a membrane port region and an open port region, whereby the bulk region has an average fluid permeability $k_b$ which is higher than the average fluid permeability $k_p$ of the membrane port region.

46 Claims, 11 Drawing Sheets

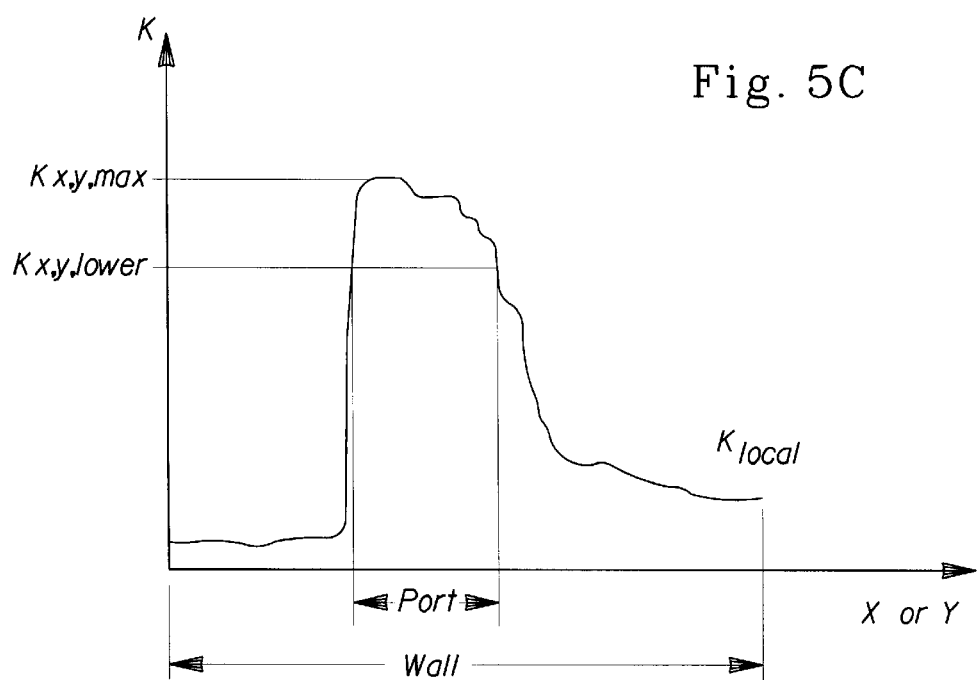

LIQUID TRANSPORT MEMBER FOR HIGH FLUX RATES BETWEEN A PORT REGION AND AN OPENING

This application is a 371 of application PCT/US99/1434, filed on Jun. 29, 1999 and claims the benefit of application PCT/US98/13449, filed on Jun. 29, 1998, application PCT/US98/13497, filed on Jun. 29, 1998, application PCT/US98/13521, filed on Jun. 29, 1998 and application PCT/US98/13523, filed on Jun. 29, 1998.

FIELD OF THE INVENTION

The present invention relates to liquid transport members useful for a wide range of applications requiring high flow and/or flux rate, wherein the liquid can be transported through such a member, and/or be transported into or out of such a member. Such members are suitable for many applications, as—without being limited to—water irrigation systems, spill absorbers, oil/water separators and the like. The invention further relates to liquid transport systems comprising said liquid transport members and articles utilizing these.

BACKGROUND

The need to transport liquids from one location to another is a well known problem.

Generally, the transport will happen from a liquid source through a liquid transport member to a liquid sink, for example from a reservoir through a pipe to another reservoir. There can be differences in potential energy between the reservoirs (such as hydrostatic height) and there can be frictional energy losses within the transport system, such as within the transport member, in particular if the transport member is of significant length relative to the diameter thereof.

For this general problem of liquid transport, there exist many approaches to create a pressure differential to overcome such energy differences or losses so as to cause the liquids to flow. A widely used principle is the use of mechanical energy such as pumps. Often however, it will be desirable to overcome such energy losses or differences without the use of pumps, such as by exploiting hydrostatic height differential (gravity driven flow), or via capillary effects (often referred to as wicking).

In many of such applications, it is desirable to transport the liquids at high rates, i.e. high flow rate (volume per time), or high flux rate (volume per time per unit area of cross-section).

Examples for applications of liquid transport elements or members can be found in fields like water irrigation such as described in EP-A-0.439.890, or in the hygiene field, such as for absorbent articles like baby diapers both of the pull-on type or with fastening elements like tapes, training pants, adult incontinence products, feminine protection devices.

A well known and widely used execution of such liquid transport members are capillary flow members, such as fibrous materials like blotting paper, wherein the liquid can wick against the gravity. Typically such materials are limited in their flow and/or flux rates, especially when wicking height is added as an additional requirement. An improvement particularly towards high flux rates at wicking heights particularly useful for example for application in absorbent articles has been described in EP-A-0.810.078.

Other capillary flow members can be non-fibrous, but yet porous structures, such as open celled foams. In particular for handling aqueous liquid, hydrophilic polymeric foams have been described, and especially hydrophilic open celled foams made by the so called High Internal Phase Emulsion (HIPE) polymerization process have been described in U.S. Pat. Nos. 5,563,179 and 5,387,207.

However, in spite of various improvements made on such executions, there is still a need to get significant increase in the liquid transport properties of liquid transport members.

In particular, it would be desired to obtain liquid transport members, that can transport liquid against gravity at very high flux rates.

In situations wherein the liquid is not homogeneous in composition (such as a solution of salt in water), or in its phases (such as a liquid/solid suspension), it can be desired to transport the liquid in its totality, or only parts thereof. Many approaches are well known for their selective transport mechanism, such as in the filter technology.

For example, filtration technology exploits the higher and lower permeability of a member for one material or phase compared to another material or phase. There is abundance of art in this field, in particular also relating to the so called micro-, ultra-, or nano-filtration. Some of the more recent publications are:

U.S. Pat. No. 5,733,581 relating to melt-blown fibrous filter;

U.S. Pat. No. 5,728,292 relates to non-woven fuel filter;

WO-A-97/47375 relating to membrane filter systems;

WO-A-97/35656 relating to membrane filter systems;

EP-A-0.780.148 relating to monolithic membrane structures;

EP-A-0.773.058 relating to oleophilic filter structures.

Such membranes are also disclosed to be used in absorbent systems.

In U.S. Pat. No. 4,820,293 (Kamme) absorbent bodies are disclosed, for being used in compresses, or bandages, having a fluid absorbent substance enclosed in a jacket made of one essentially homogeneous material. Fluid can enter the body through any part of the jacket, and no means is foreseen for liquid to leave the body.

Therein, fluid absorbent materials can have osmotic effects, or can be gel-forming absorbent substances enclosed in semipermeable membranes, such as cellulose, regenerated cellulose, cellulose nitrate, cellulose acetate, cellulose acetate butyrate, polycarbonate, polyamide, fiberglass, polysulfone, of polytetrafluoroethylene, having pore sizes of between 0.001 $\mu$m and 20 $\mu$m, preferably between 0.005 $\mu$m and 8 $\mu$m, especially about 0.01 $\mu$m.

In such a system, the permeability of the membrane is intended to be such that the absorbed liquid can penetrate, but such that the absorbent material is retained.

It is therefore desired to use membranes having a high permeability k and a low thickness d, so as to achieve a high liquid conductivity k/d of the layer, as being described herein after.

This can be achieved by incorporation of promoters with higher molecular weight (e.g., polyvinyl pyrrolidone with a molecular weight of 40,000), such that the membranes can have larger pores leading to larger membrane permeability k. The maximum pore size stated therein to be useful for this application is less than 0.5 $\mu$m, with pore sizes of about 0.01 $\mu$m or less being preferred. The exemplified materials allow the calculation of k/d values in the range of 3 to $7*10^{-14}$ m.

As this system is quite slow, the absorbent body can further comprise for rapid discharge of fluids a liquid acquisition means, such as conventional acquisition means to provide interim storage of the fluids before these are slowly absorbed.

A further application of membranes in absorbent packets is disclosed in U.S. Pat. No. 5,082,723, EP-A-0.365.565, or U.S. Pat. No. 5,108,383 (White; Allied-Signal).

Therein, an osmotic promoter, namely a high-ionic strength material such as NaCl, or other high osmolality material like glucose or sucrose is placed inside a membrane such as made from cellulosic films. As with the above disclosure, fluid can enter the body through any part of the jacket, and no means is foreseen for liquid to leave the body. When these packets are contacted by aqueous liquids, such as urine, the promoter materials provide an osmotic driving force to pull the liquid through the membranes. The membranes are characterized by having a low permeability for the promoter, and the packets achieve typical rates of 0.001 ml/cm2/min. When calculating membrane conductivity k/d values for the membranes disclosed therein, values of about 1 to $2*10^{-15}$ m result. An essential property of membranes useful for such applications is their "salt retention", i.e. whilst the membranes should be readily penetrable by the liquid, they must retain a substantial amount of the promoter material within the packets. This salt retention requirements provides a limitation in pre size which will limit liquid flux.

U.S. Pat. No. 5,082,723 (Gross et al.) discloses an osmotic material like NaCl which is enclosed by superabsorbent material, such as a copolymer of acrylic acid and sodium acrylate, thereby aiming at improving absorbency, such as enhanced absorptive capacity on a "gram per gram" basis and absorption rate.

Overall, such fluid handling members are used for improved absorbency of liquids, but have only very limited fluid transport capability.

Thus, there remains still a need to improve the liquid transport properties, in particular to increase the flow and/or flux rates in liquid transport systems.

SUMMARY OF THE INVENTION

The present invention is a liquid transport member comprising at least one bulk region and a wall region that completely circumscribes the bulk region, whereby the wall region further comprises at least one membrane port region and at least one open port region, and whereby the bulk region has an average fluid permeability $k_b$ which is higher than the average fluid permeability $k_p$ of the membrane port region. Preferably, the bulk region has a fluid permeability of at least $10^{-11}$ m², or at least $10^{-8}$ m², more preferably of at least $10^{-7}$ m², most preferably of at least $10^{-5}$ m². The membrane port region has preferably a fluid permeability of at least $6*10^{-20}$ m², or at least $7*10^{-18}$ m², more preferably of at least $3*10^{-14}$ m², even more preferably of at least $1.2*10^{-11}$ m², and even at least $7*10^{-11}$ m², most preferably of at least $10^{-9}$ m².

A liquid transport member according to the present invention further can have for the membrane port region a ratio of fluid permeability to thickness in the direction of fluid transport, $k_p/d_p$ of at least $3*10^{-15}$ m, preferably of at least $7*10^{-14}$ m, more preferably of at least $3*10^{-10}$ m, even more preferred of at least $8*10^{-8}$ m, and even preferred of at least $5*10^{-7}$ m, and most preferred of at least $10^{-5}$ m.

In a particular arrangement the liquid transport member according to the present invention is positioned such that the membrane port region is arranged above said open port region when positioned for its intended use.

In a further embodiment, a liquid transport member according to the present invention the open port region is an opening having a inner circular diameter of less than the corresponding diameter $d_b$ of a gas bubble formed in the liquid within the bulk region, or of less than 6 mm, preferably less 4 mm, more preferably less than 2 mm.

In another aspect of the present invention, a liquid transport member can have a ratio of permeability of the bulk region to the permeability of the membrane port region of at least 10, preferably at least 100, more preferably at least 1000, and even more preferably at least 10000.

In yet another aspect, a liquid transport member according to the present invention, the membrane port region has a bubble point pressure as measured with a liquid having a surface tension value of 72 mN/m of at least 1 kPa, preferably at least 2 kPa, more preferably at least 4.5 kPa, even more preferably 8 kPa, most preferably 50 kPa, or has a bubble point pressure as measured with a liquid having a surface tension value of 33 mN/m of at least 0.67 kPa, preferably at least 1.3 kPa, more preferably at least 3.0 kPa, even more preferably 5.3 kPa, most preferably 33 kPa.

A liquid transport member according to the present invention can have a bulk region which has a larger average pore size than membrane port region, preferably such that the ratio of average pore size of the bulk region and the average pore size of the membrane port region is at least 10, preferably at least 50, more preferably at least 100, and even more preferably at least 500, and most preferably at least 1000. The liquid transport member can have a bulk region with an average pore size of at least 200 μm, preferably at least 500 μm, more preferably of at least 1000 μm, and most preferably of at least 5000 μm, or with a porosity of at least 50%, preferably at least 80%, more preferably at least 90%, even more preferably of at least 98%, and most preferably of at least 99%.

In a particular design, a liquid transport member according to the present invention can be constructed by a bulk region, which is a void circumscribed by a wall region.

In a further aspects of the present invention, a liquid transport member can have a membrane port region with a porosity of at least 10%, preferably at least 20%, more preferably of at least 30%, and most preferably of at least 50%, or an average pore size of no more than 100 μm, preferably no more than 50 μm, more preferably of no more than 10 μm, and most preferably of no more than 5 μm. In another aspect, the membrane port region has a pore size of at least 1 μm, preferably at least 3 μm. Further, the membrane port region can have an average thickness of no more than 100 μm, preferably no more than 50 μm, more preferably of no more than 10 μm, and most preferably of no more than 5 μm.

In yet another aspect of the present invention, a liquid transport member can have a bulk region and a wall region having a volume ratio of at least 10, preferably at least 100, more preferably at least 1000, and even more preferably at least 10000.

In a further aspect of the present invention, a liquid transport member has a hydrophilic membrane port region, preferably by having a contact angle for the liquid to be transported less than 70 degrees, preferably less than 50 degrees, more preferably less than 20 degrees, and even more preferably less than 10 degrees. In a particular aspect, the membrane port region does not substantially decrease the liquid surface tension of the liquid that is to be transported.

In another embodiment of the present invention, a liquid transport member has an oleophilic membrane port region, preferably by having a contact angle for the liquid to be transported less than 70 degrees, preferably less than 50 degrees, more preferably less than 20 degrees, and even more preferably less than 10 degrees.

In particular embodiments, the shape of the liquid transport member can be sheet-like shape, or has a cylindrical like shape, and the membrane port region can have a larger area than the average cross-section of the member along the direction of liquid transport, preferably by at least a factor of 2, preferably a factor of 10, most preferably a factor of 100.

The liquid transport member according to the present invention can comprise a material which is expandable upon liquid contact and collapsible upon liquid removal.

In particular, the bulk region of a liquid transport member according to the present invention can comprise a material selected from the groups of fibers, particulates, foams, spirals, films, corrugated sheets, or tubes, and the wall region can comprise a material selected from the groups of fibers, particulates, foams, spirals, films, corrugated sheets, tubes, woven webs, woven fiber meshes, apertured films, or monolithic films. The foam for such embodiments can be an open cell reticulated foam, preferably selected from the group of cellulose sponge, polyurethane foam, HIPE foams, and the fibers can be made of polyolefins, polyesters, polyamids, polyethers, polyacrylics, polyurethanes, metal, glass, cellulose, cellulose derivatives.

A liquid transport member according to the present invention can be made by a porous bulk region that is wrapped by a separate wall region.

In a further embodiment of the present invention, a liquid transport member can comprise water soluble materials, such as in the port regions.

A liquid transport member according to the present invention can be adopted for the transport of water-based liquids or of viscoelastic liquids, or for the transport of oil, grease, or other non-water based liquids. Thereby, the transport can be selective for oil or grease, but not water based liquids.

In another aspect, the liquid transport member according to the present inventions, properties or parameter of the member are established prior to or at the liquid handling, preferably by activation by contact with the liquid, pH, temperature, enzymes, chemical reaction, salt concentration or mechanical activation.

In yet another aspect, the present invention relates to a liquid transport system comprising a liquid transport member as described before, and further a source of liquid and a sink of liquid that are outside the liquid transport member. In a particular aspect, the open port region is immersed in the liquid of sink or source.

A liquid transport system according to the present invention is particularly suitable for the absorption of liquids, such as having an absorption capacity of at least 5 g/g, preferably at least 10 g/g, more preferably at least 50 g/g when submitted to the Demand Absorbency Test, or by comprising sink material, that has an absorption capacity of at least 10 g/g, preferably at least 20 g/g and more preferably at least 50 g/g on the basis of the weight of the sink material, when submitted to the Teabag Centrifuge Capacity. The liquid transport system can comprise superabsorbent material or open celled foam of the High Internal Phase Emulsion (HIPE) type. Optionally, a liquid transport system can further comprise a conventional mechanical pump.

A further aspect of the present invention relates to an article comprising a liquid transport member or a liquid transport system as described before. Such an article can be suitable as a grease absorber, or as a water transport member.

DETAILED DESCRIPTION OF THE INVENTION

General Definitions

Figure 1:
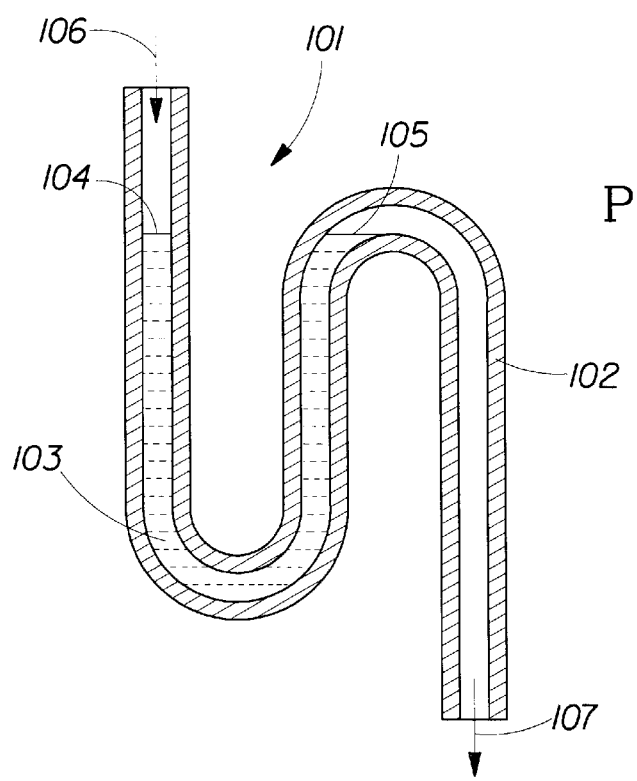
FIG. 1: Schematic diagram of conventional open siphon.

As used herein, a "liquid transport member" refers to a material or a composite of materials, which is able to transport liquids. Such a member contains at least two regions, an "inner" region, for which the term "bulk" region can be used interchangeably, and a wall region comprising at least two "port" regions, one of these being a membrane port region comprising a permeable membrane, and another one being an open port region such as an opening. The terms "inner" and "outer" refer to the relative positioning of the regions, namely meaning, that the outer region generally circumscribes the inner region, such as a wall region circumscribing a bulk region.

As used herein, the term "Z-dimension" refers to the dimension orthogonal to the length and width of the liquid transport member or article. The Z-dimension usually corresponds to the thickness of the liquid transport member or the article. As used herein, the term "X-Y dimension" refers to the plane orthogonal to the thickness of the member, or article. The X-Y dimension usually corresponds to the length and width, respectively, of the liquid transport member, or article. The term layer also can apply to a member, which—when describing it in spherical or cylindrical co-ordinates—extends in radial direction much less than in the other ones. For example, the skin of a balloon would be considered a layer in this context, whereby the skin would define the wall region, and the air filled center part the inner region.

As used herein, the term "layer" refers to a region whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered".

For purposes of this invention, it should also be understood that the term "upper" refers to members, articles such as layers, that are positioned upwardly (i.e. oriented against the gravity vector) during the intended use. For example, for a liquid transport member intended to transport liquid from a "lower" reservoir to an "upper" one, this is meant to be transport against gravity. When applying this term, for example to absorbent articles, this means that the upper elements are positioned towards the wearer during the intended use.

All percentages, ratios and proportions used herein are calculated by weight unless otherwise specified.

As used herein, the term "absorbent articles" refers to devices which absorb and contain body exudates, and, more specifically, refers to devices which are placed against or in proximity to the body of the wearer to absorb and contain the various exudates discharged from the body. As used herein, the term "body fluids" includes, but is not limited to, urine, menses and vaginal discharges, sweat and feces.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

As used herein, the term "absorbent core" refers to the component of the absorbent article that is primarily responsible for fluid handling properties of the article, including acquiring, transporting, distributing and storing body fluids. As such, the absorbent core typically does not include the topsheet or backsheet of the absorbent article.

A member or material can be described by having a certain structure, such as a porosity, which is defined by the ratio of the volume of the solid matter of the member or material to the total volume of the member or material. For example, for a fibrous structure made of polypropylene fibers, the porosity can be calculated from the specific weight (density) of the structure, the caliper and the specific weight (density) of the polypropylene fiber:

$$V_{void}/V_{total}=(1-\rho_{bulk}/\rho_{material})$$

The term "activatable" refers to the situation, where a certain ability is restricted by a certain means, such that upon release of this means a reaction such as a mechanical response happens. For example, if a spring is held together by a clamp (which thus would be activatable), releasing of the clamp results in activating the expansion of the spring. For such springs or other members, materials or systems having an elastic behavior, the expansion can be defined by the elastic modulus, as well known in the art.

Basic Principles and Definitions

Liquid Transport Mechanism in Conventional Capillary Flow Systems

Without wishing to be bound by any of the following explanations, the basic functioning mechanism of the present invention can be best explained by comparing it to conventional capillary flow materials.

In materials, for which the liquid transport is based on capillary pressure as the driving force, the liquid is pulled into the pores that were initially dry by the interaction of the liquid with the surface of the pores. Filling the pores with liquid replaces the air in these pores. If such a material is at least partially saturated and if further a hydrostatic, capillary, or osmotic suction force is applied to at least one region of that material, liquid will be desorbed from this material if the suction pressure is larger than the capillary pressure that retains the liquid in the pores of the materials (refer e.g., to "Dynamics of fluids in porous media" by J. Bear, Haifa, publ. Dover Publications Inc., NY, 1988).

Upon desorption, air will enter the pores of such conventional capillary flow materials. If additional liquid is available, this liquid can be pulled into the pores again by capillary pressure. If therefore a conventional capillary flow material is connected at one end to a liquid source (e.g., a reservoir) and on the other end to a liquid sink (e.g., a hydrostatic suction), the liquid transport through this material is based on the absorption/desorption and re-absorption cycle of the individual pores with the capillary force at the liquid/air-interface providing the internal driving force for the liquid through the material.

This is in contrast to the transport mechanism for liquids through transport members according to the present invention.

Siphon Analogy

A simplifying explanation for the functioning of the present invention can start with comparing it to a siphon (refer to FIG. 1), well known from drainage systems as a tubing in form of a laying "S" (101). The principle thereof is, that—once the tubing (102) is filled with liquid (103)—upon receipt of further liquid (as indicated by 106)—entering the siphon at one end, almost immediately liquid leaves the siphon at the other end (as indicated by 107), as—because the siphon is being filled with incompressible liquid—the entering liquid is immediately displacing liquid in the siphon forcing the liquid at the other end to exit the siphon, if there is a pressure difference for the liquid between the point of entry and the point of exit of said siphon. In such a siphon, liquid is entering and leaving the system through an open surface inlet and outlet "port regions" (104 and 105 respectively).

The driving pressure to move liquid along the siphon can be obtained via a variety of mechanisms. For example, if the inlet is at a higher position than the outlet, gravity will generate a hydrostatic pressure difference generating liquid flow through the system.

Alternatively, if the outlet port is higher than the inlet port, and the liquid has to be transported against gravity, the liquid will flow through this siphon only if an external pressure difference larger than hydrostatic pressure difference is applied. For example, a pump could generate enough suction or pressure to move liquid through this siphon. Thus, liquid flow through a siphon or pipe is caused by an overall pressure difference between its inlet and outlet port region. This can be described by well known models, such as expressed in the Bernoulli equation.

Figure 2:
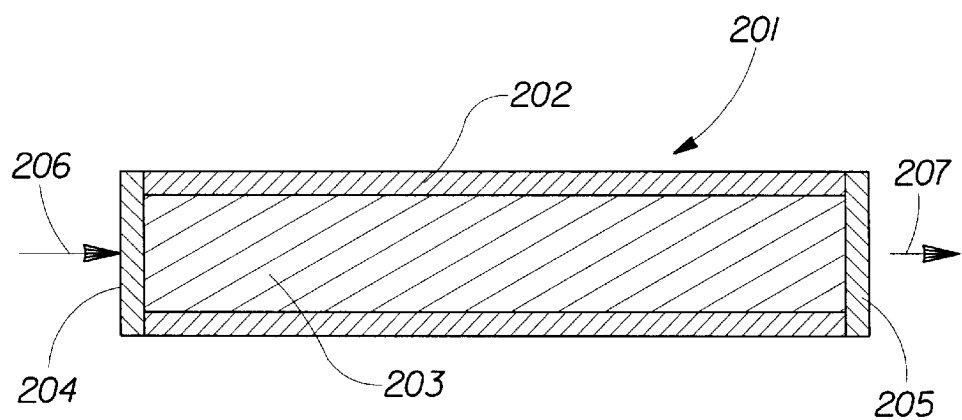
FIG. 2: Schematic diagram of a liquid transport member according to the present invention.

The analogy of the present invention to this principle is schematically depicted in FIG. 2 as one specific embodiment. Therein, the liquid transport member 201 does not need to be s-shaped, but can be a straight tube (202). The liquid transport member can be filled with liquid (203), if—as depicted in the figure—the inlet of the transport member is covered by a membrane port materials (204) and the outlet is an open port region (205), which can either be immersed in a liquid, or needs to satisfy certain requirement as discussed hereinafter. Upon receipt of additional liquid (indicated by 206) which readily penetrates through the inlet port material (204), liquid (207) will immediately leave the member through the outlet region (205), via the open outlet port region.

Thus, a key difference in principle is, that the membrane port region is not open, but satisfies special permeability requirements as explained in more detail hereinafter, which prevent air or gas from penetrating into the transport member, thus the transport member remains filled with liquid.

A liquid transport member according to the present invention can be combined with one or more liquid source(s) and/or sink(s) to form a liquid transport system. Such liquid sources or sinks can be attached to the transport member such as at inlet and/or outlet regions or the sink or the source can be integral with the member. A liquid sink can be—for example—integral with the transport member, when the transport member can expand its volume thereby receiving the transported liquid.

Figure 3A:
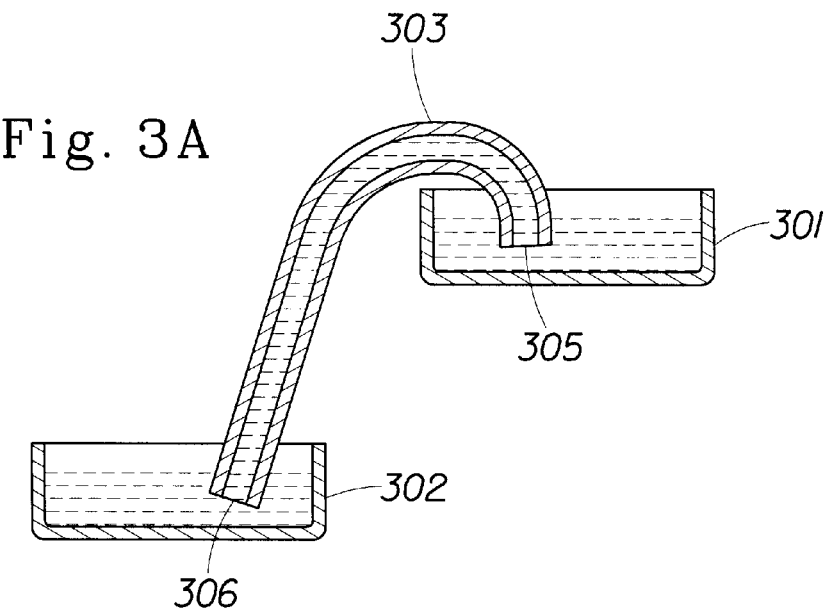
FIGS. 3A, B: Conventional Siphon system, and liquid transport member according to the present invention.
Figure 3B:
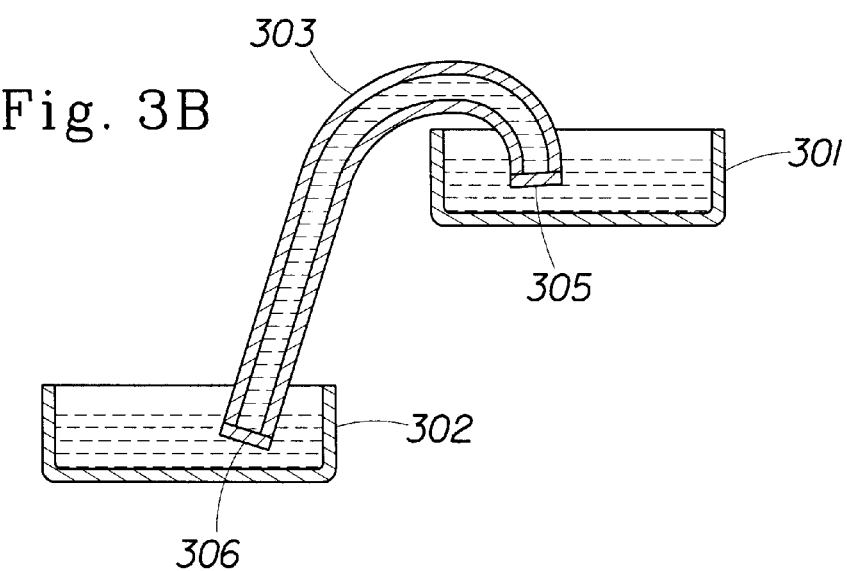

A further simplifying analogy to the a siphon system in comparison to a Liquid Transport System can be seen in FIGS. 3A (siphon) and 3B (present invention). When connecting a liquid (source) reservoir (301) with a lower (in the direction of gravity) liquid (sink) reservoir (302) by a conventional tube or pipe with open ends (303) in the shape on an inverted "U" (or "J"), liquid can flow from the upper to the lower reservoir only if the tube is kept full with liquid by having the upper end immersed in liquid. If air can enter the pipe such as by removing the upper end (305) from the liquid, the transport will be interrupted, and the tube must be refilled to be functional again.

A liquid transport member according to the present invention would look very similar in an analog arrangement, except for the ends of the transport member, inlet (305) and outlet port (306), comprising a membrane port material with special permeability requirements as explained in more detail hereinafter and only one open port region. The inlet and outlet materials prevent air or gas from penetrating into the transport member, and thereby maintain the liquid transport capability even if the inlet is not immersed into the liquid source reservoir. If the transport member is not immersed into the liquid source reservoir, liquid transport will obviously stop, but can commence immediately upon re-immersion.

In broader terms, the present invention is concerned with liquid transport, which is based upon direct suction rather than on capillarity. Therein, the liquid is transported through a region through which substantially no air (or other gas) should enter this member (or at least not in a significant amount). The driving force for liquid flowing through such a member can be created by a liquid sink and liquid source in liquid communication with the member, either externally, or internally.

There is a multitude of embodiments of the present invention, some of which will be discussed in more detail hereinafter. For example, there can be members where the inlet and/or outlet port materials are distinctly different from the inner or bulk region, or there can be members with gradual change in properties, or there can be member executions wherein the source or sink is integral with the transport member, or wherein the entering liquid is different in type or properties from the liquid leaving the member.

Yet, all embodiments rely on the inlet or outlet port region having a different permeability for the transported liquid than the inner/bulk region.

Within the context of the present invention, the term "liquid" refers to fluids consisting of a continuous liquid phase, optionally comprising a discontinuous phase such as an immiscible liquid phase, or solid or gases, so as to form suspension, emulsions or the like. The liquid can be homogeneous in composition, it can be a mixture of miscible liquids, it can be a solution of solids or gases in a liquid, and the like. Non-limiting examples for liquids that can be transported through members according to the present invention include water, pure or with additives or contaminants, salt solutions, urine, blood, menstrual fluids, fecal material over a wide ranged of consistencies and viscosities, oil, food grease, lotions, creams, and the like.

The term "transported liquid" or "transport liquid" refers to the liquid which is actually transported by the transport member, i.e., this can be the total of a homogeneous phase, or it can be the solvent in a phase comprising dissolved matter, e.g., the water of a aqueous salt solution, or it can be one phase in a multiphase liquid, or it can be that the total of the multicomponent or multiphase liquid. Henceforth, it will become readily apparent for which liquid the respective liquid properties, e.g., the surface energy, viscosity, density, etc., are relevant in for various embodiments.

Figure 4:
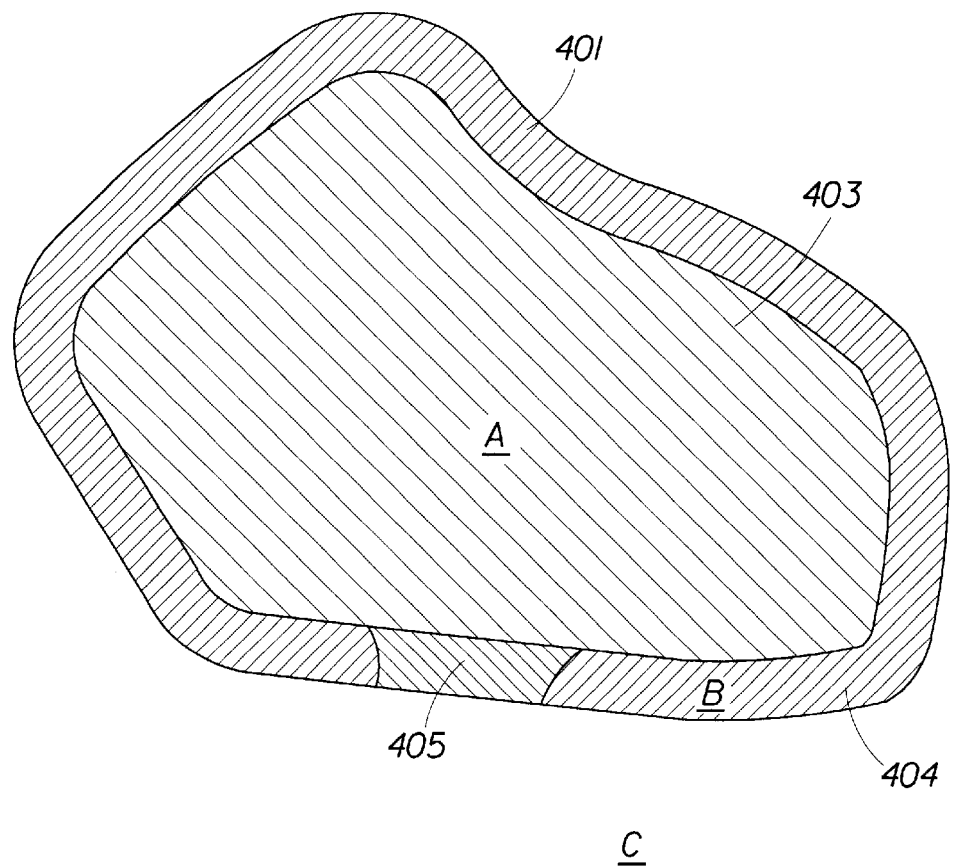
FIG. 4: Schematic cross-sectional view through a liquid transport member.

Whilst often the liquid entering the liquid transport member will be the same or of the same type as the liquid leaving the member or being stored therein, this does not necessarily need to be the case. For example when the liquid transport member is filled with an aqueous liquid, and—upon appropriate design—an oily liquid is received by the member, the aqueous phase may leave the member first. In this case, the aqueous phase could be considered "replaceable liquid", Geometric Description of Transport Member Regions A liquid transport member in the sense of the present invention has to comprise at least two regions—a "bulk region" and a "wall region" comprising at least one liquid permeable "membrane port region" and one "open port region", The geometry, and especially the requirement of the wall region completely circumscribing the bulk region is defined by the following description (refer to FIG. 4), which considers a transport member at one point in time.

The bulk/inner regions (403) and the wall region (404) are distinctively different and non-overlapping geometric regions with regard to each other as well as with regard to the outside region (i.e. "the rest of the universe"). That can be defined by the following characterization (refer to FIG. 4): Thus, any point can only belong to one of the regions.

The bulk region (403) is connected, i.e. for any two points A' and A" inside the bulk region (403), there is at least one continuous (curved or straight) line connecting the two points without leaving the bulk region (403).

For any point A inside the bulk region (403), all straight rodlike rays having a circular thickness of at least 2 mm diameter intersect the wall region (404). A straight ray has the geometrical meaning in analogy to point A being a light source, and the rays being rays of light, however, these rays need to have a minimum geometrical "thickness" (as otherwise a line can pass through the pore opening of the port regions (405)). This geometrical thickness is set at 2 mm—which of course has to be considered in an approximation in the proximity of the point A (not having a three-dimensional extension to be matched with such a rodlike ray).

The wall region (404) completely circumscribes the bulk region (403). Thus, for any points A"—belonging to the bulk region (403)—and C—belonging to the outer region—any continuous curved rod (in analogy to a continuous curved line but having circular thickness of 2 mm diameter), intersects the wall region (404).

A port region (405) connects a bulk region (403) with the outside region, and there exists at least one continuous curved rod having a circular thickness of 2 mm, that intersects the port region (405).

The term "region" refers to three-dimensional regions, which can be of any shape. Often, but not necessarily, the thickness of the region can be thin, such that the region appears like a flat structure, such as a thin film. For example, membranes can be employed in a film form, which—depending on the porosity—can have thickness of $100\,\mu m$ or much less, thus being much smaller than the extension of the membrane perpendicular thereto (i.e. length and width dimension).

A wall region may be arranged around a bulk region for example in an overlapping arrangement, i.e. that certain parts of the wall region material contact each other and are connected to each other such as by sealing. Then, this sealing should have no openings which are sufficiently large to interrupt the functionality of the member, i.e. the sealing line could be considered to belong either to an (impermeable) wall region, or a wall region.

Whilst a region can be described by having at least one property to remain within certain limits so as to define the common functionality of the subregions of this region, other properties may well change within this regions.

Within the current description, the term "regions" should be read to also encompass the term "region", i.e. if a member comprises certain "regions", the possibility of comprising only one such region should be included in this term, unless otherwise explicitly mentioned.

The "port" and "bulk/inner" regions can be readily distinguished from one another, such as a void space for one region and a membrane for another, or these regions can have a gradual transition with respect to certain relevant parameters as will be described hereinafter. Hence it is essential, that a transport member according to the present invention has at least one region satisfying the requirements for the "inner region" and one region satisfying the requirements for the "membrane port region", (which in fact can have an very small thickness relative to its extension in the other two dimensions, and thus appear more as a surface than a volume).

Thus, for a liquid transport member, the transport path can be defined as the path of a liquid entering a port region and the liquid exiting a port region, whereby the liquid transport path runs through the bulk region. The transport path can also be defined by the path of a liquid entering a port region and then entering a fluid storage region which is integral within the inner region of the transport member, or alternatively defined as the path of a liquid from a liquid releasing source region within the inner region of the transport member to an outlet port region.

The transport path of an liquid transport member can be of substantial length, a length of 100 m or even more can be contemplated, alternatively, the liquid transport member can also be of quite short length, such as a few millimeters or even less. Whilst it is a particular benefit of the present invention to provide high transport rates and also enable large amounts of liquid to be transported, the latter is not a requirement. It can also be contemplated, that only small amounts of liquid are transported over relatively short times, for example when the system is used to transmit signals in the form of liquids in order to trigger a certain response to the signal at an alternative point along the transport member.

In this case, the liquid transport member may function as a real-time signaling device. Alternatively, the transported liquid may perform a function at the outlet port, such as activating a void to release mechanical energy and create a three-dimensional structure. For example, the liquid transport member may deliver a triggering signal to a responsive device comprising a compressed material that is held in vacuum compression within a bag, at least a portion of which is soluble (e.g., in water). When a threshold level of the signaling liquid (e.g., water) delivered by the liquid transport member dissolves a portion of the water soluble region and discontinuously releases the vacuum, the compressed material expands to form a three dimensional structure. The compressed material, for example, may be a resilient plastic foam that has a shaped void of sufficient volume to capture bodily waste. Alternatively, the compressed material may be an absorbent material that functions as a pump by drawing fluid into its body as it expands (e.g., may function as a liquid sink as described below).

The liquid transport can take place along a single transport path or along multiple paths, which can split or re-combine across the transport member. Generally, the transport path will define a transport direction, allowing definition of the transport cross sectional plane which is perpendicular to said path. The inner/bulk region configuration will then define the transport cross sectional area, combining the various transport paths.

For irregularly shaped transport members and respective regions thereof, it might be necessary to average the transport cross-section over the length of the one or more transport path(s) either by using incremental approximations or differential approximations as well known from geometrical calculations.

It is conceivable, that there will be transport members, wherein the inner region and port regions are readily separable and distinguishable. In other instances, it might take more effort to distinguish and/or to separate the different regions.

Thus, when the requirements are described for certain regions, this should be read to apply to certain materials within these regions. Thereby, a certain region can consist of one homogeneous material, or a region can comprise such a homogeneous material. Also, a material can have varying properties and/or parameters, and thus comprise more than one region. The following description will focus on describing the properties and parameters for the functionally defined regions.

General Functional Description of Transport Member

As briefly mentioned in the above, the present invention is concerned with liquid transport member, which is based upon direct suction rather than on capillarity. Therein, the liquid is transported through a region into which substantially no air (or other gas) should enter (at all or at least not in a significant amount). The driving force for liquid flowing through such a member can be created by a liquid sink or liquid source in liquid communication with the transport member, either externally, or internally.

The direct suction is maintained by ensuring that substantially no air or gas enters the liquid transport member during transport. This means, that no air should enter into the transport member in significant amounts, neither through the membrane port region, which can for example be achieved by appropriately adopting the bubble point pressure, nor through the open port region, which can be achieved by immersing this open port region into a liquid reservoir, such as the sink or source of the liquid to be transported. Alternatively, if the open port region is arranged below the membrane port regions (aligned the gravity vector), the open port regions does not need to be immersed in liquid (at least not permanently) has an opening sufficiently small to not allow air to enter the member therethrough.

Thus, a liquid transport member must have a certain liquid permeability (as described hereinafter). A higher liquid permeability provides less flow resistance, and thus is preferred from this point of view.

The liquid transport member according to the present invention has an inner region with a liquid permeability which is relatively high to provide minimum flow resistance. The permeability of a membrane port region, which can be a part of the wall region circumscribing the bulk region, is substantially less. This is achieved by port regions having a membrane functionality, designed for the intended use conditions. The membrane is permeable to fluids, but not to gases or vapors. Such a property is generally expressed by the bubble point pressure parameter, which is—in short—defined by the pressure up to which gas or air does not penetrate through a wetted membrane.

As will be discussed in more detail, the property requirements have to be fulfilled at the time of liquid transport. It can be, however, that these are created or adjusted by activating a transport member, e.g., prior to usage, which—without or prior to such activation—would not satisfy the requirements but so after activation. For example, a member can be elastically compressed or collapsed, and expand upon wetting to then create a structure with the required properties.

For one aspect of the present invention, there are at least three regions within the transport member with different pore sizes, namely at least one membrane port region having smaller pore sizes (at least one open port region, and an inner region having a substantially larger pore sizes compared to the membrane port region.

The membrane port region should have a relatively high bubble point pressure. In this aspect of the invention, the high bubble point pressure of the port region is obtained by the capillary pressure of the small pores of said port region which will—once wetted—prevent from air or gas from entering the transport member.

In another aspect, the present invention is concerned with liquid transport members, which—once activated, and/or wetted—are selective with regards to the fluids they transport. The membrane port region of the transport member is—up to a certain limit as can be expressed by the bubble point pressure—closed for the ambient gas (like air), but relatively open for the transport liquid (like water).

The port region does not require a specific directionality of its properties, i.e. the membrane materials used therein can be used in either orientation of liquid flow there through. Nor is it a requirement for the membranes to have different properties (such as permeability) with regard to certain parts or components of the liquid. This is in contrast to the membranes such as described for osmotic absorbent packets in U.S. Pat. No. 5,108,383 (White et al.), where the membranes have to have a low permeability for the promoter material, such a salt, respectively salt-ions.

Bulk Region

In the following section, the requirements as well as specific executions for the "inner region" or "bulk region" will be described.

A key requirement for the bulk region is to have a low average flow resistance, such as expressed by having a permeability k of at least $10^{-11}$ m$^2$, preferably more than $10^{-8}$ m$^2$, more preferably more than $10^{-7}$ m$^2$, and most preferably more than $10^{-5}$ m$^2$. One important means to achieve such high permeabilities for the inner regions can be achieved by utilizing material providing relatively high porosity.

Such a porosity, which is commonly defined as the ratio of the volume of the materials that makes up the porous materials to the total volume of the porous materials, and as determined via density measurements commonly known, should be at least 50%, preferably at least 80%, more preferably at least 90%, or even exceeding 98%, or 99%. In the extreme of the inner region essentially consisting of a single pore, void space, the porosity approaches or even reaches 100%.

The inner region can have pores, which are larger than about 200 μm, 500 μm, 1 mm or even 9 mm in diameter or more. For certain applications, such as for irrigation or oil separation, the inner region can have pores as large as 10 cm—e.g. when the inner region is a void tube.

Such pores may be smaller prior to the fluid transport, such that the inner region may have a smaller volume, and expand just prior or at the liquid contact. Preferably, if such pores are compressed or collapsed, they should be able to expand by a volumetric expansion factor of at least 5, preferably more than 10. Such an expansion can be achieved by materials having an elastic modulus of more than the external pressure which, however, must be smaller than the bubble point pressure.

High porosities can be achieved by a number of materials, well known in the art as such. For example fibrous members can readily achieve such porosity values. Non-limiting examples for such fibrous materials that can be comprised in the bulk region are high-loft non-wovens, e.g., made from polyolefin or polyester fibers as used in the hygienic article field, or car industry, or for upholstery or HVAC industry. Other examples comprise fiber webs made from cellulosic fibers.

Such porosities can further be achieved by porous, open celled foam structures, such as—without intending any limitation—for example pulyurethane reticulated foams, cellulose sponges, or open cell foams as made by the High Internal Phase Emulsion Polymerization process (HIPE foams), all well known from a variety of industrial applications such as filtering technology, upholstery, hygiene and so on.

Such porosities can be achieved by wall regions (such as explained in more detail hereinafter) which circumscribe voids defining the inner region, such as exemplified by pipes. Alternatively, several smaller pipes can be bundled.

Such porosities can further be achieved by "space holders", such as springs, spacer, particulate material, currugated structures and the like.

The inner region pore sizes or permeabilities can be homogeneous throughout the inner region, or can be inhomogeneous.

It is not necessary, that the high porosity of the inner region is maintained throughout all stages between manufacture and use of the liquid transport member, but the voids within the inner region can be created shortly before or during its intended use.

For example, bellow like structures held together by suitable means can be activated by a user, and during its expansion, the liquid penetrates through a port region into the expanding inner region, thereby filling the transport member completely or at least sufficiently to not hinder the liquid flow.

Alternatively, open celled foam materials, such as described in (U.S. Pat. No. 5,563,179 or U.S. Pat. No. 5,387,207) have the tendency to collapse upon removal of water, and the ability to re-expand upon re-wetting. Thus, such foams can be transported from the manufacturing site to the user in a relatively dry, and hence thin (or low-volume), and only upon contact with the source liquid increase their volume so as to satisfy the void permeability requirements.

The inner regions can have various forms or shapes. The inner region can be cylindrical, ellipsoidal, sheet like, stripe like, or can have any irregular shape.

The inner regions can have constant cross-sectional area, with constant or varying cross-sectional shape, like rectangular, triangular, circular, elliptical, or irregular. A cross-sectional area is defined for the use herein as a cross-section of the inner region, prior to addition of source liquid, when measured in the plane perpendicular to the flow path of the transport liquid, and this definition will be used to determine the average inner region cross-sectional area by averaging the individual cross-sectional areas all over the flow path(s).

The absolute size of the inner region should be selected to suitably match the geometric requirements of the intended use. Generally, it will be desirable to have the minimum dimension for the intended use. The benefit of the designs according to the present invention is to allow much smaller cross-sectional areas than conventional materials. The dimensions of the inner region are determined by the permeability of said inner region, which can be very high, due to possible large pores, as the inner region does not have to be designed under the contradicting requirements of high flux (i.e. large pores) and high vertical liquid transport (i.e. small pores). Such large pemeabilities allow much smaller cross-sections, and hence very different designs.

Also the length of the inner region can be significantly larger than for conventional systems, as also with regard to this parameter the novel transport member can bridge longer distances and also greater vertical liquid transport heights.

The inner region can be essentially non-deformable, i.e. maintains its shape, form, volume under the normal conditions of the intended use. However, in many uses, it will be desirable, that the inner region allows the complete member to remain soft and pliable.

The inner region can change its shape, such as under deforming forces or pressures during use, or under the influence of the fluid itself. The deformability or absence thereof can be achieved by selection of one or more materials in the inner region (such as a fibrous member), or can be essentially determined by the circumscribing regions, such as by the wall regions of the transport member. One such approach is to utilize elastomeric materials as the wall material.

The voids of the inner region can be confined by wall regions only, or the inner region can comprise internal separations therein.

If, for example, the inner region is made up of parallel pipes, with impermeable cylindrical walls, these would be considered to be such internal separations, thereby possibly creating pores which are unitary with the inner, hollow opening of the pipes, and possibly other pores created by the interstitial spaces between the pipes. If, as a further example, the inner region comprises a fibrous structure, the fiber material can be considered to form such internal separations.

The internal separations of the inner region can have surface energies adapted to the transported liquid. For example, in order to ease wetting and/or transport of aqueous liquids, the separations or parts thereof can be hydrophilic. Thus, in certain embodiments relating to the transport of aqueous liquids, it is preferred to have the separations of the inner regions to be wettable by such liquids, and even more preferred to have adhesion tensions of more than 65 mN/m, more preferably more than 70 mN/m. In case of the transported liquid is oil based, the separations or parts thereof can be oleo- or lipophilic.

The confining separations of the inner region may further comprise materials which significantly change their properties upon wetting, or which even may dissolve upon wetting. Thus, the inner region may comprise an open cell foam material having a relatively small pore at least partially being made of soluble material, such as polyvinylalcohol or the like. The small porosity can draw in liquid at the initial phase of liquid transport, and then rapidly dissolve so as to then leave large voids filled with liquid.

Alternatively, such materials may fill larger pores, completely or partially, For example, the inner region can comprise soluble materials, such as poly(vinyl) alcohol or poly(vinyl)acetate. Such materials can fill the voids, or support a collapsed state of the voids before the member is contacted with liquid. Upon contact with fluid, such as water, these materials may dissolve and thereby create empty or expanded voids.

In one embodiment, the voids of the inner region (which can make up essentially the complete inner region) are essentially completely filled with an essentially incompressible fluid.

The term "essentially completely" refers to the situation, where sufficient void volume of the inner region is filled with the liquid such that a continuous flow path can be established.

Preferably, most of the void volume, preferably more than 90%, more preferably more than 95%, and even more preferably more than 99%, including 100%, is filled with the liquid. The inner region can be designed so as to enhance accumulation of gas or other liquid in parts of the region where it is less detrimental. The remainder of the voids can then be filled with other fluid, such as is residual gas or vapors, or immiscible liquid like oil in an inner region filled with aqueous liquids, or can be solids, like particulates, fibers, films.

The liquid comprised in the inner region can be of the same type as the liquid being intended to be transported. For example, when water based liquids are the intended transported medium, the inner region of the transport member can be filled with water—or if oil is the intended transport liquid, the inner region can be filled with oil.

The liquid in the inner region can also be different—whereby these differences can be relatively small in nature (such as when the intended transport liquid is water, the inner region liquid can be an aqueous solution, and vice versa). Alternatively, the intended transport liquid can be quite different in its properties, when compared to the liquid which has been pre-filled into the inner region, such as when the source liquid is oil, which is transported through a pipe initially filled with water and closed by suitable inlet and outlet ports, whereby the water leaves the member by a suitable outlet port region, and the oil enters the member by a suitable inlet port region. In this specific embodiment, the total amount of transported liquid is limited by the amount which can be received within the member respectively the amount of liquid exchanged, unless there were, for example, outlet port regions comprising materials with properties compatible with the liquids so as to allow functionality with one or both of the liquids.

The liquid of the inner region and the liquid to be transported can be mutually soluble, such as salt solutions in water. For example, if the liquid transport member is intended for the transport of blood or menses, or an oily liquid, the inner region can be filled with water.

In another embodiment, the inner region comprises a vacuum, or a gas or vapor below the corresponding equilibrium, ambient or external, pressure at the respective temperatures, and volumetric conditions. Upon contact with the transported liquid, the liquid can enter into the inner region by the permeable port regions (as described hereinafter), and then fill the voids of the inner region to the required degree. Thereafter, the now filled inner region functions like a "pre-filled" region as described in the above.

The above functional requirements and structural embodiments of the inner region can be satisfied by a number of suitable structures. Without being limited in creating structures satisfying suitable inner regions, the following describes a range of preferred embodiments.

A simple and yet very descriptive example for an inner region is an empty tube defined by impermeable or semi-permeable walls and a further opening submersed in a liquid, as already indicated in FIG. 2. The diameter of such tubes can be relatively large compared to diameters commonly used for transport in capillary systems. The diameter of course depends highly on the specific system and intended use.

Also suitable is the a porous material, or a combination of parallel tubes of a suitable diameter such as from about 0.2 mm to several cm to a tube bundle, such as (in principle) known from other engineering design principles such as heat exchanger systems.

For certain applications, pieces of glass tubes can provide the right functionality, however, for certain applications such structures may have some mechanical strength constraints. Suitable tubes can also be made of silicon, rubber, PVC, etc., e.g., Masterflex 6404-17 by Norton, distributed by the Barnant Company, Barrington, Ill. 60010 U.S.

Yet another embodiment can be seen in the combination of mechanically expanding elements, such as springs or which can open void space in the structure if the expansion direction is oriented such that the appropriate pore size is also oriented along the flow path direction.

Such materials are well known in the art, and for example disclosed in U.S. Pat. Nos. 5,563,179, 5,387,207, 5,632,737 all relating to HIPE foam materials, or in U.S. Pat. No. 5,674,917 relating to absorbent foams, or in EP-A-0.340.763, relating to highly porous fibrous structures or sheets, such as made from PET fibers.

Other materials can be suitable even when they do not satisfy all the above requirements at the same time, if this deficiency can be compensated by other design elements.

Other materials having relatively large pores are highloft non-woven, filter materials as open cell foams from Recticel in Brussel, Belgium such as Bulpren, Filtren (Filtren TM10 blue, Filtren TM20 blue, Filtren TM30 blue, Filtren Firend 10 black, Filtren Firend 30 black, Filtren HC 20 grey, Filtren Firend HC 30 grex, Bulpren S10 black, Bulpren S20 black, Bulpren S30 black).

A further embodiment to exemplify a material with two pore size regions can be seen in PCT application US97/20840, relating to a woven loop structure.

The inner region may further be constructed from several materials, i.e. for example from combinations of the above.

The inner region may also comprise stripes, particulates, or other in-homogeneous structures generating large voids between themselves and acting as space holders.

As will be described in more details for the port regions, the fluids in the inner region must not prevent the port regions from being filled with the transport liquid.

Wall Region

The liquid transport member according to the present invention comprises in addition to the inner region a wall region circumscribing this inner region. This wall region must comprise at least one membrane port region and an open port region, as described hereinafter. The wall region can further comprise materials, which are essentially impermeable to liquids and/or gases, thereby preventing ambient gases or vapors from penetrating into the liquid transport member.

Such walls can be of any structure or shape, and can re present the key structural element of the liquid transport member. Such walls can be in the shape of a straight or bent pipe, of a flexible pipe, or of cubical shape and so on. The walls can be thin, flexible films, circumscribing the inner region. Such walls can be expandable, either permanently via deformation or elastically via elastomeric film, or upon activation.

Whilst the wall regions as such are an essential element for the present invention, this is particularly true for the port region comprised in such walls, and described in the following. The properties of the remaining parts of the wall region can be important for the overall structure, for resilience, and other structural effects.

Membrane Port Region(s)

The membrane port region can generally be described to comprise materials which have different permeabilities for different fluids, namely they should be permeable for the transport liquid, but not for the ambient gas (like air), under otherwise same conditions (like temperature, or pressure, ...) and once they are wetted with/filled with the transport liquid or similarly functioning liquid.

Often, such materials are described as membranes with respective characteristic parameters.

In the context of this invention, a membrane is generally defined as a region, that is permeable for liquid, gas or a suspension of particles in a liquid or gas. The membrane may for example comprise a microporous region to provide liquid permeability through the capillaries. In an alternative embodiment, the membrane may comprise a monolithic region comprising a block-copolymer through which the liquid is transported via diffusion.

For a given set of conditions, membranes will often have selective transport properties for liquids, gases or suspensions depending on the type of medium to be transported. They are therefore widely used in filtration of fine particles out of suspensions (e.g. in liquid filtration, air filtration). Other type of membranes show selective transport for different type of ions or molecules and are therefore found in biological systems (e.g. cell membranes, molecular sieves) or in chemical engineering applications (e.g. for reverse osmosis).

Microporous hydrophobic membranes will typically allow gas to permeate, while water-based liquids will not be transported through the membrane if the driving pressure is below a threshold pressure commonly referred to as "breakthrough" or "bridging" pressure.

In contrast, hydrophilic microporous membranes will transport water based liquids. Once wetted, however, gases (e.g. air) will essentially not pass through the membrane if the driving pressure is below a threshold pressure commonly referred to as "bubble point pressure".

Hydrophilic monolithic films will typically allow water vapor to permeate, while gas will not be transported rapidly through the membrane.

Similarly, membranes can also be used for non-water based liquids such as oils. For example, most hydrophobic materials will be in fact oleophilic. A hydrophobic microporous membrane will therefore be permeable for oil but not for water and can be used to transport oil, or also separate oil and water.

Membranes are often produced as thin sheets, and they can be used alone or in combination with a support layer (e.g. a nonwoven) or in a support element (e.g. a spiral holder). Other forms of membranes include but are not limited to polymeric thin layers directly coated onto another material, bags, corrugated sheets.

Further known membranes are "activatable" or "switchable" membranes that can change their properties after activation or in response to a stimulus. This change in properties might be permanent or reversible depending on the specific use. For example, a hydrophobic microporous layer may be coated with a thin dissolvable layer e.g. made from poly(vinyl)aclohol. Such a double layer system will be impermeable to gas. However, once wetted and the poly (vinyl)alcohol film has been dissolved, the system will be permeable for gas but still impermeable for liquid.

Conversely, if a hydrophilic membrane is coated by such a soluble layer, it might become activated upon liquid contact to allow liquid to pass through, but not air.

In another example, a hydrophilic microporous membrane is initially dry. In this state the membrane is permeable for air. Once wetted with water, the membrane is no longer air permeable. Another example for a reversible switching of a membrane in response to a stimulus is a microporous membrane coated with a surfactant that changes its hydrophilicity depending on temperature. For example the membrane will then be hydrophilic for warm liquid and hydrophobic for cold liquid. As a result, warm liquid will pass through the membrane while cold liquid will not. Other examples include but are not limited to microporous membranes made from an stimulus activated gel that changes its dimensions in response to pH, temperature, electrical fields, radiation or the like.

Properties of Membrane Port Region

The membrane port region can be described by a number or properties and parameters.

A key aspect of the membrane port region is the permeability.

The transport properties of membranes may in general be described by a permeability function using Darcy's law which is applicable to all porous systems:

$$q = 1/A * dV/dt = k/\eta * \Delta p/L$$

Thus, a volumetric flow dV/dt through the membrane is caused by an external pressure difference Δp (driving pressure), and the permeability function k may depend on the type of medium to be transported (e.g. liquid or gas), a threshold pressure, and a stimulus or activation. Further relevant parameters impacting on the liquid transport are the cross-section A and the length L of the transport region, and the viscosity η of the transported liquid.

For porous membranes, the macroscopic transport properties are mainly depending on the pore size distribution, the porosity, the tortuosity and the surface properties such as hydrophilicity.

If taken alone, the permeability of the membrane port region should be high so as to allow large flux rates there through. However, as permeability is intrinsically connected to other properties and parameters, typical permeability values for port region or port region materials will range from about $6*10^{-20}$ m$^2$, to $7*10^{-18}$ m$^2$, or $3*10^{-14}$ m$^2$, up to $1.2*10^{10}$ m$^2$ or more.

A further parameter relevant for the membrane port region and respective materials is the bubble point pressure, which can be measured according to the method as described hereinafter.

Suitable bubble point pressure values depend on the type of application in mind. The table below lists ranges of suitable port region bubble point pressure (BPP) for some applications, as determined for respective typical fluids:

| | BPP (kPa) | |
| --- | --- | --- |
| Application | broad range | typical range |
| Irrigation | <2 to >50 | 8 to 50 |
| Grease absorption | 1 to 20 | 1 to 5 |
| Oil Separation | <1 to about 50 | |

In a more general approach, it has been found useful, to determine the BPP for a material by using a standardized test liquid, as described in the test methods hereinafter.

Membrane Port Region Thickness and Size

The membrane port region of a liquid transport member is defined as the part of the wall having the highest permeability, when disregarding the open port region as described hereinafter. The membrane port region is also defined by having the lowest relative permeability when looking along a path from the bulk region to a point outside the transport member.

Figure 5A:
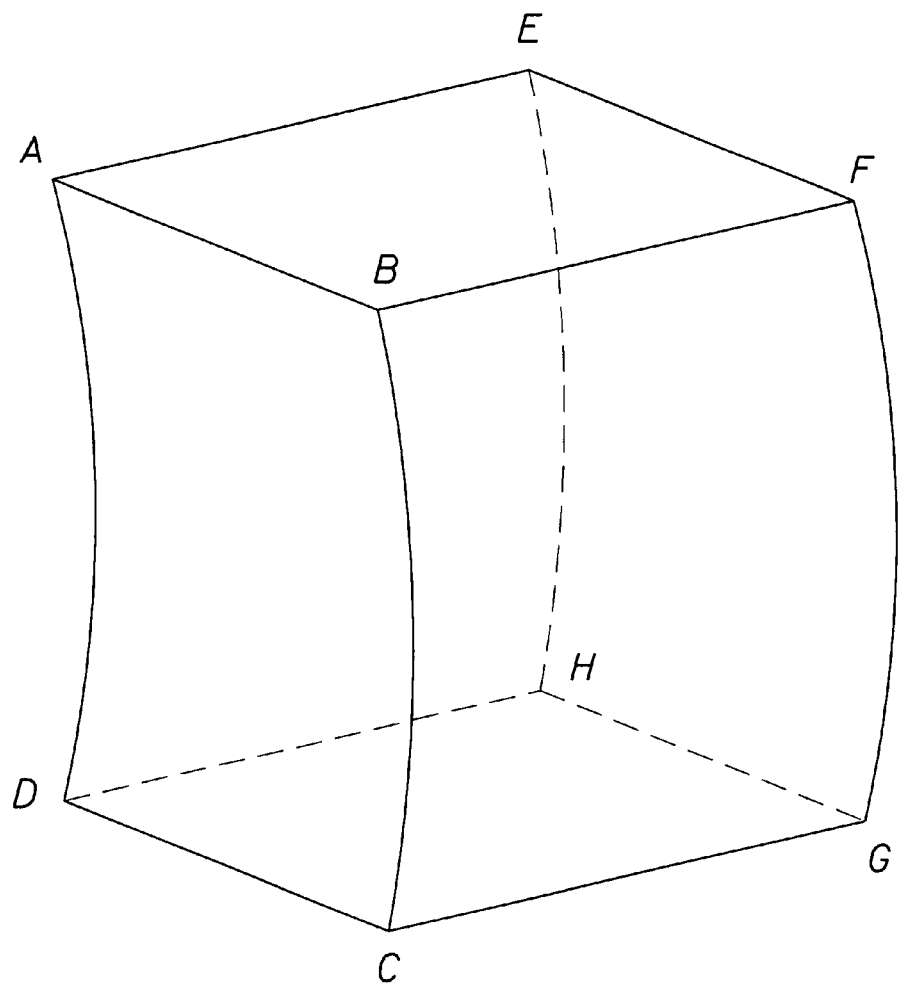
FIGS. 5A, B, C: Schematic representation for the determination of port region thickness.
Figure 5A:
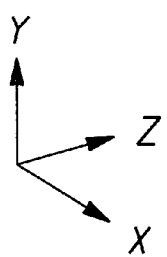

The membrane port region can be constructed by readily discernible materials, and then both thickness and size can be readily determined. The membrane port region can, however, have a gradual transition of its properties either to other, impermeable regions of the wall region, or to the bulk region. Then the determination of the thickness and of the size can be made as described hereinafter. When looking at a segment of the wall region, such as depicted in FIG. 5A, this will have a surface, defined by the cornerpoints ABCD, which is oriented towards the inner or bulk region, and a surface EFGH oriented towards the outside of the member. Thus the thickness dimension is oriented. along the lines AE, BF, and so on, i.e. when using Cartesian co-ordinates, along the z-direction. Analogously, the wall region will have the major extension along the two perpendicular directions, i.e. x-, and y-direction.

Figure 5B:
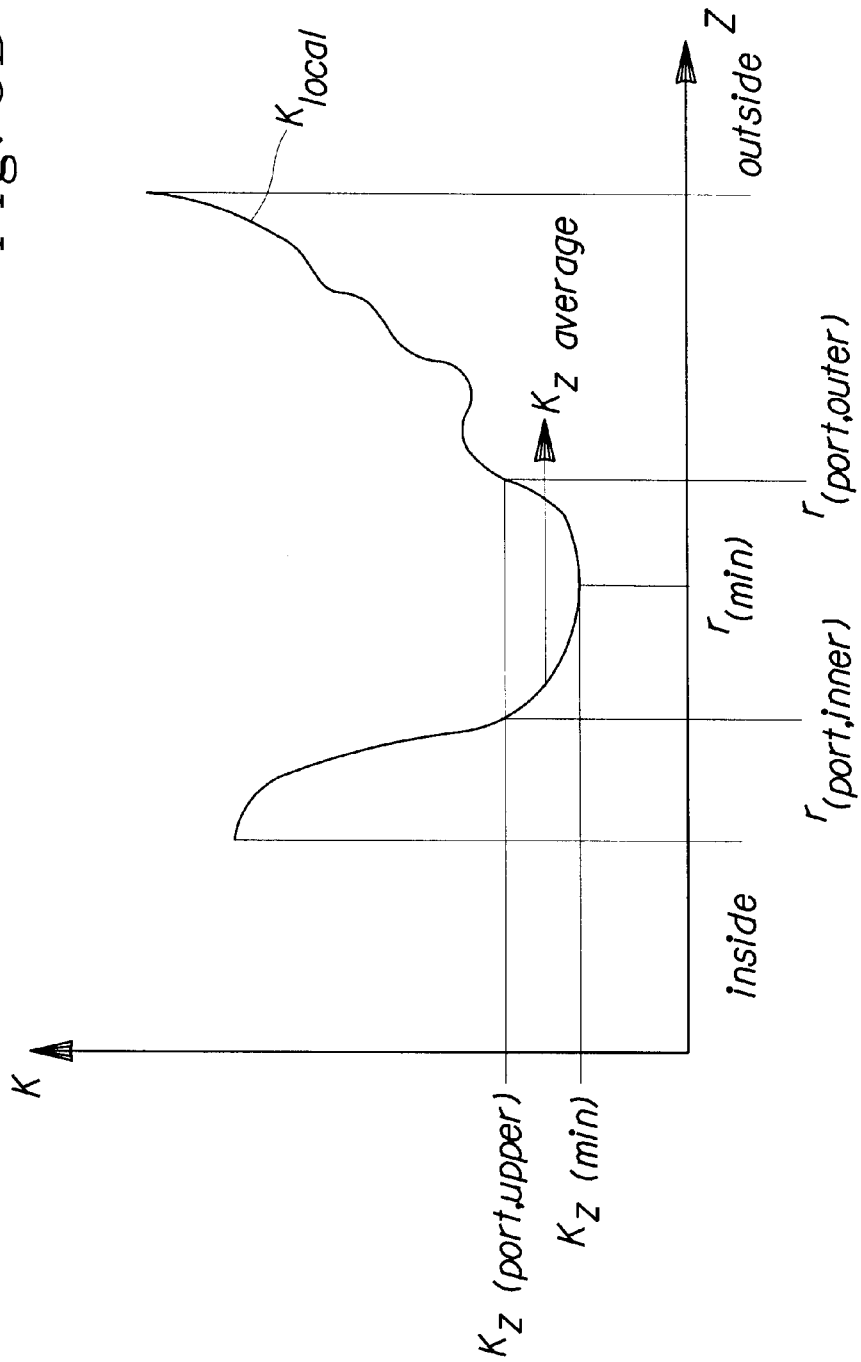
Figure 6:
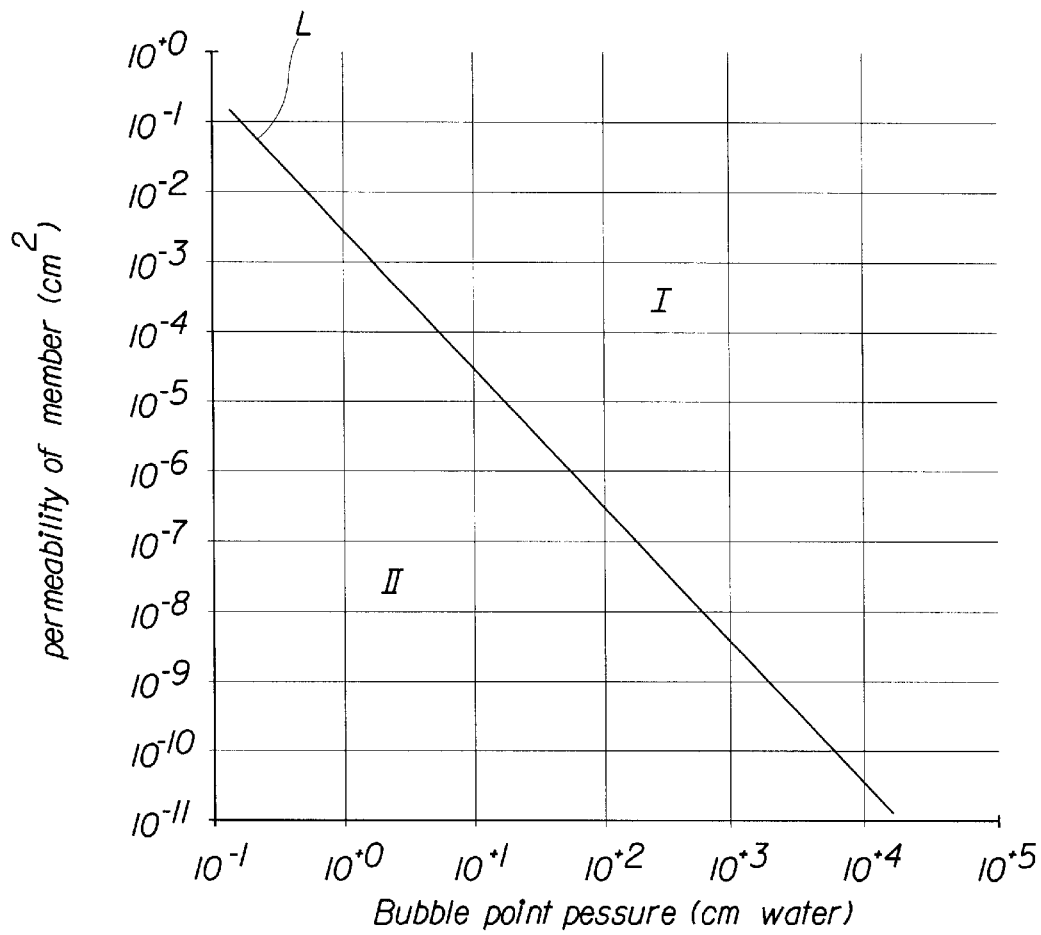
FIG. 6: Correlation of permeability and bubble point pressure.
Figure 7A:
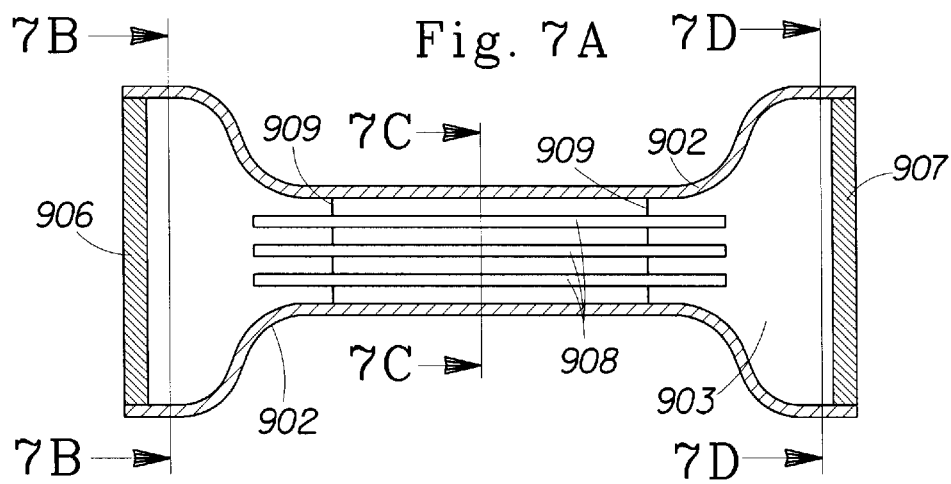
FIGS. 7A, 7B, 7C, 7D, 8A and 8B: Schematic diagrams of various embodiments of liquid transport member according to the present invention.
Figure 7C:
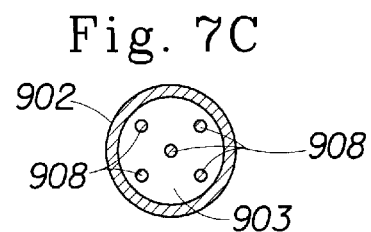
Figure 7B:
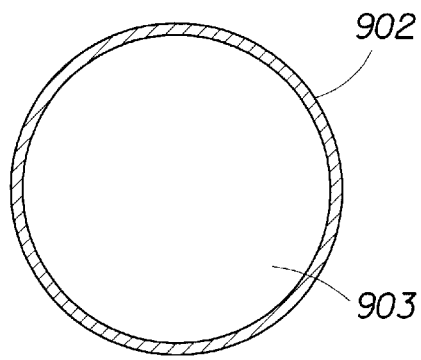
Figure 7D:
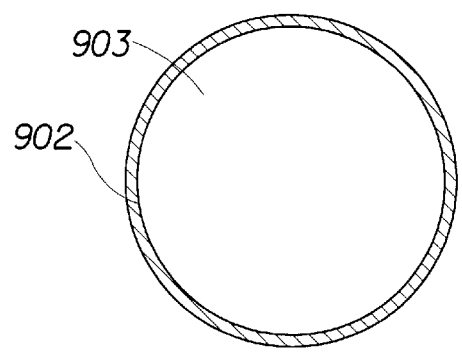

Then, the membrane port region thickness can be determined as follows:
a) In case of essentially homogeneous port region properties at least in the direction through the thickness of the region, it is the thickness of a material having such a homogeneous permeability (such as when a membrane film);
b) It is the thickness of the membrane if this is combined with a carrier (be this carrier inside or outside of the membrane)—i.e. this refers to a non-continuous/step change function of the properties along this path;
c) For a material having a (determinable) continuous gradient permeability across any segment as in FIG. 5A, the following steps can be taken to reach a determinable thickness (refer to FIG. 5B):
c0) First, a permeability profile is determined along the z-axis, and the curve $k_{[local]}$ vs r is plotted; for certain members, the porosity or pore size curve can also be taken for this determination with appropriate changes of the subsequent procedure.
c1) Then the point of lowest permeability ($k_{min}$ is determined, and the corresponding length reading ($r_{[min]}$) is taken.
c2) As the third step, the "upper port region permeability" is determined as being 10 times the value of $k_{min}$.
c3) As the curve has a minimum at $k_{min}$ there will be two corresponding $r_{inner}$ and $r_{outer}$, defining the inner and outer limit of the membrane port region respectively.
c4) The distance between the two limits defines the thickness, and the average $k_{port,\ average}$ will be determined across this.

If this approach fails due to indeterminable gradient permeability, porosity or pore size, the thickness of the membrane port region will be set to 1 micrometer.

As indicated in the above, it will often be desirable to minimize the thickness of the membrane port region, respectively the membrane materials comprised therein. Typical thickness values are in the range of less than 100 μm, often less than 50 μm, 10 μm, or even less than 5 μm.

Quite analogous, the x-y extension of the membrane port region can be determined. In certain liquid transport member designs it will be readily apparent, which part of the wall region are membrane port regions. In other designs, with gradually changing properties across the wall region, the local permeability curves along the x- and y direction of the wall region can be determined, and plotted analogous to FIG. 5B as shown in FIG. 5C. In this instance, however, the maximum permeability in the wall region defines the membrane port region, hence the maximum will be determined, and the region having permeabilities of not less than a tenth of the maximum permeability surrounding this maximum is defined as the membrane port region.

Yet another parameter useful for describing aspects of the membrane port region useful for the present invention is the permeability to thickness ratio, which in the context of the present invention is also referred to as "membrane conductivity".

This reflects the fact, that—for a given driving force—the amount of liquid penetrating through a material such as a membrane is on one side proportional to the permeability of the material, i.e. the higher the permeability, the more liquid will penetrate, and on the other side inversely proportional the thickness of the material.

Henceforth, a material having a lower permeability compared to the same material having a decrease in thickness, shows that thickness can compensate for this permeability deficiency (when regarding high rates a being desirable).

Thus, this parameter can be very useful for designing the membrane port region materials to be used.

Suitable k/d depends on the type of application in mind. The table below lists ranges of typical k/d for some exemplary applications:

| Application | k/d ($10^{-a}$ m) typical range |
|---|---|
| Irrigation | 1 to 300 |
| Grease absorption | 100 to 500 |
| Oil Separation | 1 to 500 |

The membrane port region has to be wettable by the transport fluid, and the hydrophilicity or lipophilicity should be designed appropriately, such as by using hydrophilic membranes in case of transporting aqueous liquids, or hydrophobic membranes in case of lipophilic or oily liquids.

The surface properties in the membrane port region can be permanent, or they can change with time, or usage conditions.

It is preferred, that the receding contact angle for the liquid to be transported is less than 70°, more preferably less than 50°, even more preferred less than 20° or even less than 10°. Further, it is preferred, that the material has no negative impact on the surface tension of the transported liquid.

For example, a lipohilic membrane may be made from lipophilic polymers such as polyethylene or polypropylene and such membranes will remain liphophilic during use.

Another example is a hydrophilic material allowing aqueous liquids to be transported. If a polymer like polyethylene or polypropylene is to be used, this has to be hydrophilized, such as by surfactants added to the surface of the material or added to the bulk polymer, such as adding a hydrophilic polymer prior to forming the membrane port material. In both instances, the imparted hydrophilicity may be permanent or not, e.g. it could be washed away with the transport liquid passing therethrough. However, as it is an important aspect of the present invention, that the membrane port region remain in a wetted state so as to prevent gas passing through, the lack of hydrophilizer will not be significant once the membrane port region are wetted.

Maintaining Liquid Filling of Membrane

For a porous membrane to be functional once wetted (permeable for liquid, not-permeable for air) at least a continuous layer of pores of the membrane always need to be filled with liquid and not with gas or air. Thus, it can be desirable for particular applications to minimize the evaporation of the liquid from the membrane pores, either by a decrease of the vapor pressure in the liquid or by an increase the vapor pressure in the air. Possible ways to do this include—without any limitation:

Sealing of the membrane with a impermeable wrap to avoid evaporation between production and usage. Use of strong desiccants (e.g. $CaCl_2$) in the pores, or use of a liquid with low vapor pressure in the pores that mixes with the transported fluid.

Alternatively, the membrane port region may be sealed with soluble polymers, such as poly vinyl alcohol, or poly vinyl acetate, which are dissolved upon contact with liquids and which thereby activate the functionality of the transport member.

Apart from the liquid handling requirements, the membrane port region should satisfy certain mechanical requirements.

First, the membrane port region should not have any negative effect on the intended use conditions. For example when such members are intended in hygienic absorbent articles, the comfort and safety must not be negatively impacted.

Thus it will often be desirable, that the membrane port region are soft, and flexible, but this may not always be the case. However, the membrane port region should be sufficiently strong to withstand practical use stress, such as tear stress or puncturing stress or the like.

In certain designs, it might be desirable for the membrane port region materials to be extensible or collapsible, or bendable.

A single hole in the membrane (e.g. caused by puncturing during use), a failure in membrane sealing (e.g. owing to production), or the membrane tearing (e.g. due to in-use pressure being exerted) can lead to a failure of the liquid transport mechanism. Whilst this can be used as a destructive test method to determine if a materials or member functions according the present invention, this is not desirable during its intended use. If air or another gas penetrates into the inner region, this may block the liquid flow path within the region, or it may also interrupt the liquid connection between the bulk and port region.

A possibility to make an individual member more robust, is to provide in certain parts of the inner region remote from the main liquid flow path, a pocket where air that enters the system is allowed to accumulate without rendering the system non functional.

A further way to address this issue is to have several liquid transport member in a (functionally or geometrically) parallel arrangement instead of a single liquid transport member. If one of the members fails, the others will maintain the functionality of the "liquid transport member battery".

The above functional requirements of the membrane port region can be satisfied by a wide range of materials or structures described by the following structural properties or parameters.

The pore structure of the region, respectively of the materials therein, is an important parameter impacting on properties like permeability and bubble point pressure.

Two key aspects of the pore structure are the pore size, and pore size distribution. A suitable method to characterize these parameters at least on the surface of the region is by optical analysis.

As has been discussed above in the context of permeability, permeability is influenced by the pore size and the thickness of the region, respectively the part of the thickness which is predominantly determining the permeability.

Henceforth, it has been found, that for example for aqueous systems typical average pore size values are in the range of 0.5 to 500 μm. Thus the pores have preferably an average size of less than 100 μm, preferably less than 50 μm, more preferably less than 10 μm or even less than 5 μm. Typically, these pores are not smaller than 1 μm.

It is an important feature for example of the bubble point pressure, that this will depend on the largest pores in the region, which are in a connected arrangement therein. For example, having one larger pore embedded in small ones does not necessarily harm the performance, whilst a "cluster" of larger pores together might very well do so. Henceforth, it will be desirable to have narrow pores size distribution ranges.

Another aspect relate to the pore walls, such as pore wall thickness, which should be a balance of openess and strength requirements. Also the pores should be well connected to each other, to allow liquid passing through readily.

As some of the preferred port region materials can be thin membrane materials, these in themselves may have relatively poor mechanical properties. Henceforth, such membranes can be combined with a support structure, such as a coarser mesh, a non-woven or the like.

Such a support structure could be combined with the membrane such that it is positioned towards the inner/bulk region or towards the outside of the member.

Size/surface Area of Membrane Port Region

The size of the membrane port region is essential for the overall performance of the transport member, and needs to be determined in combination with the "permeability to thickness" $(k/d)_{ratio}$ of the membrane port region.

The size has to be adapted to the intended use, so as to satisfy the liquid handling requirements. Generally, it will be desirable to have the liquid handling capability of the inner/bulk region and the membrane port region be compatible, such that neither is a grossly limiting factor for liquid transport compared to the other. As for a given driving force the flux (i.e. the flow rate through a unit area) of the membrane port region will generally be lower than the flux through the inner region, it may be preferred to design the membrane port region relatively thin in thickness and/or larger in size (surface) than the cross-section of the inner region.

Thereby, the exact design and shape of the membrane port region can vary over a wide range. For example, when the amount of tranported liquid per time unit is relatively slow—such as for providing a trigger or signal from one port region to another, or for providing rather a controlled liquid flow, such as can be desirable for irrigation systems—the membrane port region can be relatively Membranes, Polyvinyldifluorid films, non-wovens, woven materials such as meshes made from metal, or polymers as m Polyamide, or Polyester. Other suitable materials can be apertured Films, such as vacuum formed, hydroapertured, mechanically or Laser apertured, or films treated by electron, ion or heavy-ion beams.

Specific materials are Cellulose acetate membranes, such as also disclosed in U.S. Pat. No. 5,108,383 (White, Allied-Signal Inc.), Nitrocellulose membranes such as available from e.g. from Advanced Microdevices (PVT) LTD, Ambala Cantt. INDIA called CNJ-10 (Lot # F030328) abd CNJ-20 (Lot # F 024248). Cellulose acetat membranes, Cellulose nitrate membrances, PTFE membrances, Polyamide membranes,Polyester membranes as available e.g. from Sartorius in Göttingen, Germany and Millipore in Bedford USA, can be very suitable. Also microporous films, such as PE/PP film filled with $CaCO_3$ particles, or filler containing PET films as disclosed in EP-A-0.451.797.

Other embodiments for such port region materials can be ion beam apertured polymer films, such as made from PE such as described in "Ion Tracks and Microtechnology—Basic Principles and Applications" edited by R. Spohr and K. Bethge, published by Vieweg, Wiesbaden, Germany 1990.

Other suitable materials are woven polymeric meshes, such as polyamide or polyethylene meshes as available from Verseid ag in Geldem-Waldbeck, Germany, or SEFAR in Rüschlikon, Switzerland. Other materials which can be suitable for present applications are hydrophilized wovens, such as known under the designation DRYLOFT® from Goretex in Newark, DE 19711, USA.

Further, certain non-woven materials are suitable, such as available under the designation CoroGard® from BBA Corovin, Peine, Germany, can be used, namely if such webs are specially designed towards a relatively narrow pore size distribution.

For applications with little requirements for flexibility of the members, or where even a certain stiffness is desirable, metal filter meshes of the appropriate small, such as about the size of the cross-section of the inner region, such that a substantially smaller transport member results.

Alternatively, when large amounts of liquids are to be quickly captured and transported, distributed or stored, the member can be shaped for example in the shape of a dog bone with relatively large membrane port region at either end of the transport member or, the membrane port region can be spoon shaped so as to increase the receiving area.

Alternatively, the membrane port region can be non-flat, such as for example corrugated, or folded, or having other forms so as to create relative large surface area to volume ratios.

The membrane port region properties may be constant over time, or they may change with time, such as being different before and during use.

For example, the membrane port region can have properties unsuitable for functioning in members according to the present invention until the point of use. The membrane port region may be activated, for example by manual activation, intervention by the person using the member, or by an automatic activation means, such as by wetting of the transport member. Other alternative mechanisms for activation of the membrane port region can include temperature change, for example from an ambient temperature to the body temperature of a wearer, or pH, for example of the transport liquid, or an electrical or mechanical stimulus.

As has been discussed in the context of osmotic packet materials in the above, membranes useful for the present invention have no specific requirement of a certain salt impermeability.

Whilst the membrane port regions and suitable materials have been described with regard to their properties or descriptive parameters, the following will describe some of the materials that satisfy these various requirements, thereby focusing on the transport of aqueous liquids.

Suitable materials can be open celled foams, such as High Internal Phase Emulsion foams, can be Cellulose Nitrate Membranes, Cellulose Acetate pore size can be suitable, such as HIGHFLOW of Haver & Böcker, in Oelde, Germany Open Port Region In addition to the membrane port region, the liquid handling member according to the present invention comprises at least an open port region. This region can generally be represented by an opening having a dimension significantly larger than the pores of the membrane port region have.

In one embodiment of the present invention, the functionality of the liquid transport member is maintained as long as this opening is not exposed to air, i.e., it is effectively closed by a liquid into which the part of the liquid transport member comprising the opening is immersed. Thus, the open port region can be immersed into a liquid reservoir, from which liquid is removed through the liquid transport member having the membrane port connected to a liquid sink. Conversely, the open port region can be immersed in a liquid receiving reservoir, into which liquid can be transported from a liquid source in contact with the membrane port region. The open port region can be of any suitable shape and dimension, obviously sufficiently large to not significantly impede the liquid transport.

A particular embodiment of the present invention comprises an open port region with one or more openings still being significantly larger than the pores of the membrane port regions, but being sufficiently small to not allow gas bubble generation into the inner region at the opening. This is of course depending on the fluids.

For aqueous liquids, and for horizontally oriented openings, the dimension should be not more than the bubble size as can be approximated by the well known bubble formation formula (see e.g. Chem.Eng. Handbook, Perry/Chilton, McGraw-Hill, 5$^{th}$ edition, 1973, equation 18–128)

$$d_b = (6 * d_o / (g * \rho_1))^{1/3}$$

wherein $d_b$ is the bubble diameter of the generated gas bubble in mm;

$d_o$ denotes the diameter of the opening in mm;

g denotes the gravity constant;

and $\rho_1$ denotes the density of the liquid (neglecting the density of the gas) as expressed in [mm].

For typical aqueous systems, an opening has preferably an inner circumscribing diameter of less than about 6 mm, preferably less than about 4 mm and more preferably less than about 2 mm, whereby the diameter is defined by the largest circle, which can be inscribed the opening. If the open port region is not aligned horizontally, the opening can larger, and—for example for a flexible tube bent into the horizontal plane (thus providing a vertically oriented opening extending into the horizontal part of the tube, which then can bend upwardly), openings up to 12 mm have been found to function satisfactorily. If the opening is shaped irregularly, (for example as by having a star like shape), the corresponding diameter is the one of the largest inscribing circle, which can be geometrically put into the opening. If more than one openings exist, each will be considered as one open port region.

For such designs, gas will not enter the system even if the open port region is removed from the liquid reservoir, or the liquid level in the reservoir is reduced too much, as long as the open port region is positioned lower with regard to the direction of gravity than the membrane port region or—in more general terms—the pressure inside the member close to the membrane is lower than the surrounding pressure outside the membrane.

One and the same structure may at one point in time have an open port immersed in liquid (such as a filled reservoir), and thus would need to satisfy the requirements for the first embodiment, but at another point in time (such as when the reservoir became empty) it would not be immersed in liquid, and the requirements of the second embodiment would need to be satisfied to ensure the maintenance of the liquid transport member functionality upon provision of liquid in the reservoir.

Additional Elements

Whilst the definition of bulk, wall, and outer region has been made in the above in relation to the function of each of these regions, there may optionally elements be added to the materials forming these regions, which can extend into a neighbouring region without extending the liquid handling functionality, but rather improve other properties, such as the mechanical strength, or tactile or visual aspects of the materials forming the regions or of the complete structure. For example, a support structure may be added to the outside of the wall or port region, which may be so open that it does not impact on the fluid handling properties, and as such would be considered functionally to belong to the outer region. When such an open support element extends from the wall region into the inner or bulk region, it will functionally belong to the bulk region. If there is a gradual transition between these materials and/or elements, the definitions made for the respective functional regions will enable a clear distinction of the region forming materials, and the additional elements.

In addition to the inner/bulk and wall regions, the liquid transport member according to the present invention can optionally contain other elements, such as liquid impermeable walls or separations, in addition to the wall region with one or more port regions.

Further, there can be additional elements outside of the wall regions, such as materials to provide enhanced physical strength, or improved tactile feel or the like. Whilst such external elements might be arranged such that liquid flows there-through, they do not contribute to the essential functionality of the liquid transport member. Thus, such elements should not be a flow limiting factor, and may not function as a port region. Such elements can be integral with the wall region.

Further, there can be elements attached to or integral with the liquid transport member to aid its implementation into an absorbent system, or an article comprising an liquid transport member.

Relative Permeability

If the permeability of both the inner/bulk region and the membrane port region can be determined independently, it is preferred that the membrane port region has a lower liquid permeability than the inner region.

Thus, a liquid transport member should have a ratio of the permeability of the bulk region to the membrane port region of preferably at least 10:1, more preferably at least 100:1, even more preferably at least 1000:1, even ratios of 10000:1 are acceptable.

Relative Arrangement of Regions

Depending on the specific embodiments, there can be various combinations of the inner, the wall, membrane port region, and open port region.

At least a portion of the membrane port region has to be in liquid communication with the inner region, so as to allow fluid to be transferred thereto. The open port region will also be in direct contact with the inner region, as will naturally occur through an opening.

The pore size ratio of inner region pores to membrane port region pores are preferably at least 10:1, more preferably at least 30:1, even more preferably at least 100:1 and most preferable at least 350:1.

The area of the membrane port region will typically be larger than the cross-section of the inner regions. In most instance, the membrane port region will be twice as large as the inner region cross-section, often four times as large, or even 10 times as large.

Structural Relation of Regions

The various regions can have similar structural properties or different, possibly complementing, structural properties, such as strength, flexibility, and the like.

For example, all regions can comprise flexible material designed to cooperatively deform, whereby the inner region comprises a thin-until-wet material which expands upon contact with the transported liquid, the membrane port region comprise flexible membranes, and the walls can be made of liquid impermeable flexible film having an opening representing the open port region.

The liquid transport member can be made of various materials, whereby each region may comprise one or more materials. For example, the inner region may comprise porous materials, the walls may comprise a film material, and the membrane port may comprise a membrane material. Alternatively, the transport member may consist essentially of one material with different properties in various regions, such as a foam with very large voids to provide the functionality of the inner region, with membrane type materials to function as membrane port materials.

In an embodiment as depicted in FIG. 7, the liquid transport member may comprise several inlet and/or several outlet port regions, for example as can be achieved by connecting a number of tubes (802) together and closing several end openings with inlet ports 806 or an outlet port 807, whereby either the inlet or the outlet ports are open port regions, thereby circumscribing the inner region 803, or a "split" system where fluid is transported simultaneously to more than one location (more than one exit port). Alternatively, the transport to different locations may be selective (e.g., the voids in a transport material on the route to one port may be filled with a water soluble material, and the voids in the transport material on the route to a second port may be filled with an oil soluble material. Also, the transport medium may be hydro- and/or oleo-philic to further enhance the selectivity.)

Figure 8A:
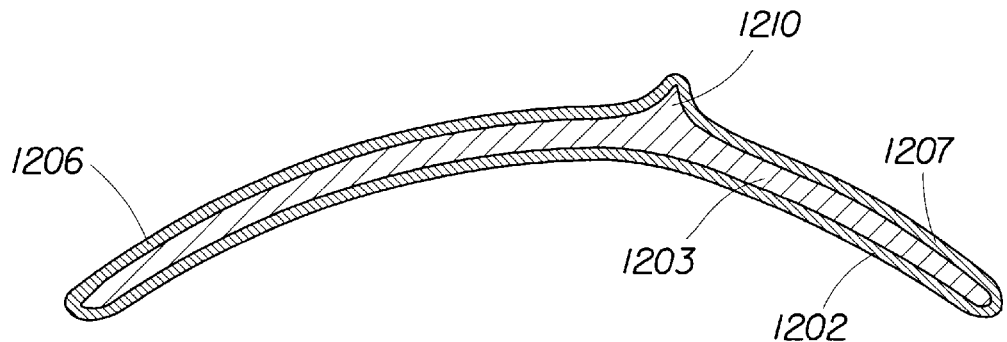
Figure 8B:
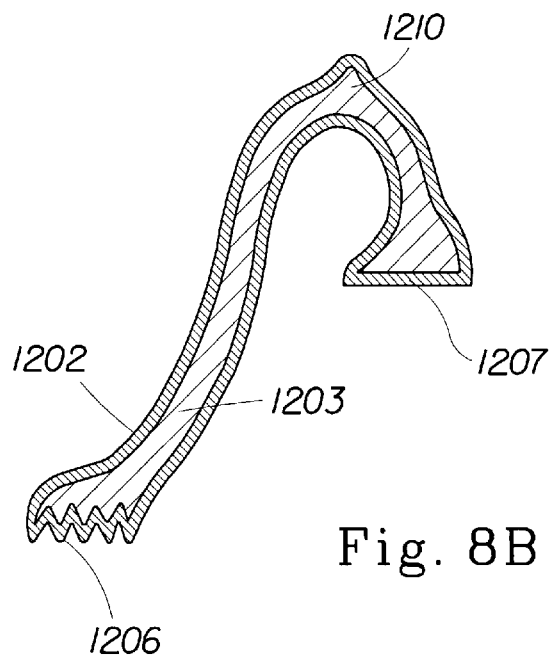

In a particular embodiment, the inner region can be void of liquid at the beginning of the liquid transport process (i.e. contains a gas at a pressure less than the ambient pressure surrounding the liquid transport member). In such cases, the liquid supplied by a liquid source can penetrate through the membrane port region or the open port regions to fill the voids of the membrane and the inner region. In another embodiment, where the membrane port region comprises a liquid soluble material, the first liquid contacting this member can first dissolve this soluble material and thereafter wet the membrane. In such an instance, the inner regions may not be completely filled with the transport fluid, but a certain amount of residual gas or vapor may be retained. If the gas or vapor is soluble in the transported liquid, it is possible that after some liquid passes through the member, that substantially all of the initially present gas or vapor is removed, and the inner region becomes substantially free of gass. In cases with some residual gas or vapor being present in the inner region, this may reduce the effective available cross-section of the fluid member, unless specific measures are taken, such as indicated in FIG. 8, with wall region (1202) comprising membrane port region (1206) and open port region (1207) circumscribing the inner region (1203) and with region (1210) to allow gas to accumulate.

In further embodiments of the present invention, one or more of the above described embodiments can be combined.

Liquid Transport System

The following describes suitable arrangement of such a liquid transport member to create a suitable Liquid Transport System (LTS) according to the present invention.

A Liquid Transport System within the scope of the present invention comprises the combination of at least one liquid transport member with at least one further liquid sink or source in liquid communication with the member.

The source can be any form of free liquid or loosely bound liquid so as to be readily available to be received by the transport member.

For example a pool of liquid, or a freely flowing volume of liquid, or an open porous structure filled with liquid.

The sink can be any form of a liquid receiving region. In certain embodiments, it is preferred to have the liquid more tightly bound than the liquid in the liquid source. The sink can also be an element or region containing free liquid, such that the liquid would be able to flow freely or gravity driven away from the member. Alternatively, the sink can contain absorbent, or superabsorbent material, absorbent foams, expandable foams, alternatively it can be made of a spring activated bellows system, or it can contain osmotically functioning material, or combinations thereof.

Liquid communication in this context refers to the ability of liquids to transfer or to be transferred from the sink or source to the member, such as can be readily achieved by contacting the elements, or bringing the elements so closely together, that the liquid can bridge the remaining gap.

Such a liquid transport system comprises a liquid transport member according to the above description plus at least one liquid sink or source. The term at least applies to systems, where the liquid transport member itself can store or release liquids, such that a liquid transport system comprises a sink and a liquid releasing liquid transport member; or a source and a liquid receiving liquid transport member; or a sink and a source and a liquid transport member.

In each of these options, the liquid transport member can have liquid releasing or receiving properties in addition to a sink or source outside of the member.

At least a portion of the membrane port region must be in liquid communication with the source liquid and where applicable the sink material. One approach is to have the membrane port region material form the outer surface of the liquid transport member, in part or as the whole outer surface, so as to allow liquids such as liquids of the liquid source or sink to readily contact the membrane port region. The effective port region size can be determined by the size of the liquid communication with the sink or source respectively. For example, the total of the membrane port region can be in contact with the sink or source, or only a part thereof.

In one embodiment of the present invention, the functionality of the liquid transport member is maintained as long as this opening is not exposed to air, i.e., it is effectively closed by a liquid into which the part of the liquid transport member comprising the opening is immersed. A further embodiment of the present invention comprises an open port region with one or more openings still being significantly larger than the pores of the membrane port regions, but being sufficiently small to not allow gas bubble generation into the inner region at the opening, such that for this embodiment, the open port region may under the above described conditions be removed from the liquid reservoir.

It will be apparent, that a sink must be able to receive liquid from the member (and where applicable from the respective port regions), and a source must be able to release liquid to the member (and where applicable to the respective port regions).

Henceforth, a liquid source for a liquid transport member according to the present invention can be a free flowing liquid, such as urine released by a wearer, or a open water reservoir.

A liquid source region can also be an intermediate reservoir, such as a liquid acquisition member in absorbent articles.

Analogously, a liquid sink can be a free flow channel, or an expanding reservoir, e.g., a bellowed element combined with mechanical expansion or spacer means, such as springs.

A liquid sink region can also be an ultimate liquid storage element of absorbent members, such as being useful in absorbent articles and the like.

In a preferred embodiment, a liquid transport system has an absorption capacity of at least 5 g/g, preferably at least 10 g/g, more preferably at least 50 g/g and most preferably at least 75 g/g on the basis of the weight of the sink material, when measured in the Demand Absorbency Test as described hereinafter.

In yet another preferred embodiment, the liquid transport system contains a sink comprising an absorbent material having an absorption capacity of at least 10 g/g, preferably at least 20 g/g and more preferably at least 50 g/g, on the basis of the weight of the liquid transport system, when measured in the Teabag Centrifuge Capacity Test as described hereinafter.

In yet a further preferred embodiment, and the liquid transport system comprises an absorbent material providing an absorbent capacity of at least 5 g/g, preferably at least 10 g/g, more preferably of at least 50 g/g or most preferably of at least 75 g/g up to the a capillary suction corresponding to the bubble point pressure of the member, especially of at least 4 kPa, preferably at least 10 kPa, when submitted to the known Capillary Sorption test as described in co-pending PCT patent application US98/13497, filed on Jun. 29, 1998. Such materials exhibit preferably a low capacity in the capsorption test above the bubble point pressure, such as 4 kPa or even 10 kPa, of less than 5 g/g, preferably less than 2 g/g, more preferably less than 1 g/g, and most preferably less than 0.2 g/g.

In certain specific embodiments, the liquid transport member also contains superabsorbent materials or foam made according to the High Internal Phase Emulsion polymerization, such as described in PCT application US98/05044. Typically, the suction of the liquid sink material will not exceed the bubble point pressure of the port region.

Applications

There is a wide field for applying liquid transport members or systems according to the present invention. The following should not be seen to be limiting in any way, but rather to exemplify areas, where such members or systems are useful.

Other suitable applications can be found for a bandage, or other health care absorbent systems. In another aspect, the article can be a water transport system or member, optionally combining transport functionality with filtration functionality, e.g. by purifying water which is transported. Also, the member can be useful in cleaning operation, so as by removing liquids or as by releasing fluids in a controlled manner. A liquid transport member according to the present invention can also be a oil or grease absorber.

One specific application can be seen in self-regulating irrigation systems for plants. Thereby, the inlet port can be immersed into a reservoir, and the transport member can be in the form of a long tube. In contrast to known irrigation systems (such as known under BLUMAT as available from Jade @ National Guild, PO Box 5370, Mt Crested Butte, Colo. 81225), the system according to the present invention will not loose its functionality upon drying of the reservoir, but remain functional until and after the reservoir is refilled.

A further application can be seen in air conditioning systems, with a similar advantage as described for the irrigation systems. Also, because of the small pore sizes of the port regions, this system would be easier to clean than conventional wetting aids, such as porous clay structures, or blotter paper type elements.

Yet a further application is the replacement of miniature pumps, such as can be envisaged in biological systems, or even in the medical field.

An even further application can be seen in selective transport of liquids, such as when aiming at transporting oil away from an oil/water mixture. For example, upon oil spillages on water, a liquid transport member can be used to transfer the oil into a further reservoir. Alternatively, oil can be transported into a liquid transport member comprising therein a sink functionality for oil.

An even further application uses the liquid transport member according to the present invention as a transmitter for a signal. In such an application, the total amount of transported liquid does not need to be very large, but rather the transport times should be short. This can be achieved, by having a liquid filled transport member, which upon receipt of even a little amount of liquid at the inlet port practically immediately releases liquid at the outlet port. This liquid can then be used to stimulate further reaction, such as a signal or activated a response, e.g., dissolving a seal to release stored mechanical energy to create a three dimensional change in shape or structure.

An even further application exploits the very short response times of liquid transport and practically immediate response time.

Method of Making Liquid Transport Members

The liquid transport members according to the present invention can be produced by various methods, which have to have in common the essential steps of combining a bulk or inner region with a wall region comprising port regions with appropriate selection of the respective properties as described in the above. This can be achieved by starting from a homogeneous material, and imparting therein different properties. For example, if a member is a polymeric foam material, this can be produced form one monomer with varying pore sizes, which will then be polymerized to form a suitable member.

This can also be achieved by starting from various essentially homogeneous materials and combining these into the a member. In this execution, a wall material can be provided, which may have homogeneous or varying properties, and a bulk material can be provided, which can be open porous material, or a void space can be defined to represent the bulk region. The two materials can the be combined my suitable techniques, such as by wrapping or enveloping as well known in the art, such that the wall material completely circumscribes the bulk region or bulk region material.

In order to enable liquid transport, the bulk region can be filled with liquid, or can be subjected to vacuum, or can be equipped with other aids so as to created vacuum, or liquid filling.

Optionally, the method of forming a member according to the present invention can comprise the step of applying activation means, which can be of the mechanical type. This activation means can also comprise materials which react upon the transport liquid, such as dissolve. Such materials may be applied in the port regions, e.g. to open the port regions upon use, or such materials may be applied to the bulk regions, such as to allow expansion of these regions upon wetting.

The making of members according to the present invention can be done in an essentially continuous way, such as by having various materials provided in roll form, which are then unwound and processed, or any of the materials can be provided in discrete form, such as foam pieces, or particulates.

EXAMPLES

The following section provides specific suitable examples for liquid transport members and systems according to the present invention, thereby starting by describing various samples suitable for being used in certain regions of these members or systems.

S-1 Samples Suitable for Membrane Port Regions
S-1 Samples Suitable for Port Regions
- S-1.1:—Woven filter mesh HIFLO ®, type 20 such as available from Haver & Boecker, Oelde, Germany, made from stainless steel, having at a porosity of 61%, and a caliper of 0.09 mm, designed for filtering down to 19 $\mu$m to 20 $\mu$m.
- S-1.2a:—Polyamide mesh Monodur Type MON PA 20 N such as available from Verseidag in Geldern-Waldbeck, Germany.
- S-1.2b: Polyamide mesh Monodur Type MON PA 42.5 N such as available from Verseidag in Geldem-Waldbeck, Germany.
- S-1.3a: Polyester mesh such as 07-20/13 of SEFAR in Rüschlikon, Switzerland.
- S-1.3b: Polyamide mesh 03-15/10 of SEFAR in Rüschlikon, Switzerland.
- S-1.3c: Polyamide mesh 03-20/14 of SEFAR in Rüschlikon, Switzerland.
- S-1.3d: Polyamide mesh 03-1/1 of SEFAR in Rüschlikon, Switzerland.
- S-1.3e: Polyamide mesh 03-5/1 of SEFAR in Rüschlikon, Switzerland.
- S-1.3f: Polyamide mesh 03-10/2 of SEFAR in Rüschlikon, Switzerland.
- S-1.3g: Polyamide mesh 03-11/6 of SEFAR in Rüschlikon, Switzerland.
- S-1.4: Cellulose acetate membranes such as described in U.S. Pat. No. 5,108,383 (White, Allied-Signal Inc.).
- S-1.5: HIPE foam produced according to the teachings of U.S. patent application Ser. No. 09/042,429, filed Mar. 13, 1998 by T. DesMarais et al. titled "High Suction polymeric foam", the disclosure of which is incorporated herein by reference.
- S-1.6: Nylon Stockings e.g. of 1.5 den type, commercially available in Germany, such as from Hudson.

S-2 Samples Suitable for Wall Regions not Representing Port Regions
- S-2.1: Flexible adhesive coated film, such as commercially available under the trade name "d-c-fix" from Alkor, Gräfelfing, Germany.
- S-2.2: Plastic funnel Catalog # 625 617 20 from Fisher Scientific in Nidderau, Germany.
- S-2.3: Flexible tubing (inner diameter about 8 mm) such as Masterflex 6404-17 by Norton, distributed by the Bamant Company, Barrington, Ill. 60010 U.S.A.
- S-2.4: Conventional polyethylene film such as used as backsheet material in disposable diapers, such as available from Clopay Corp., Cincinnati, Ohio, US, under the code DH-227.
- S-2.5: Conventional polyethylene film such as used as backsheet material in disposable diapers, such as available from Nuova Pansac SpA in Milano, Italy under the code BS code 441118.
- S-2.6: Flexible PVC tube e.g. Catalog # 620 853 84 from Fisher Scientific in Nidderau, Germany.
- S-2.7: PTFE Tube e.g. Catalog # 620 456 68 from Fisher Scientific in Nidderau, Germany.

S-3 Samples Suitable Inner Region
- S-3.1: Void as created by any stiff wall/port region.
- S-3.2: Metallic springs having a outer diameter of 4 mm and a length of about 6 cm with any applied force, as available from Fedemfabrik Dietz in Neustadt, Germany under the designation "federn" article # DD/100.
- S-3.3: Open cell foams from Recticel in Brussels, Belgium such as Filtren TM10 blue, Filtren TM20 blue, Filtren TM30 blue, Filtren Firend 10 black, Filtren Firend 30 black, Filtren HC 20 grey, Filtren Firend HC 30 grex, Bulpren S10 black, Bulpren S20 black, Bulpren S30 black).
- S-3.4: HIPE foams as produced according to the teachings of U.S. patent application Ser. No. 09/042,418, filed Mar. 13 1998 by T. DesMarais et al., titled "Absorbent Materials For Distributing Aqueous Liquids", the disclosure of each of which is incorporated by reference herein.
- S-3.5: Particulate pieces of S-3.4 or S-3.3.

S-4 Samples for Pressure Gradient Creation Means
- S-4.1: Osmotic pressure gradient materials according to the teachings of U.S. Pat. No. 5,108,383 (White, Allied Signal).
- S-4.2: Height difference between inlet and outlet generating a hydrostatic height generated pressure difference.
- S-4.3: Various partially saturated porous materials (Absorbent foams, superabsorbent materials, particles, sand, soils) generating a capillary pressure difference.
- S-4.4: Difference in air pressure at the inlet and the outlet as e.g. generated by a vacuum pump (airtight sealed) to the outlet.

Example A For Transport Member
Combination of wall region with port region, inner region filled with liquid:
- A) A ca 20 cm long tube (S-2.6) is connected in an air tight way with a glass funnel (S-2.2). Sealing can be made with Parafilm M (available from Fischer Scientific in Nidderau, Germany catalog number 617 800 02). A circular piece of port material (S-1.1), slightly larger than the open area of the funnel is sealed in an air tight way with the funnel. Sealing is made with suitable adhesive, e.g., Pattex™ of Henkel KGA, Germany.

Example B for Transport System (i.e. Member and (Source and/or Sink))
- B) To exemplify an application of a liquid transport system, the liquid transport member of A has been positioned between a liquid source reservoir and a flower pot, such that a portion of the inlet port region is immersed in the liquid reservoir, and the outlet port being put into the soil of the flower pot. The relative height of the reservoir and the flower pot is of no relevance for this length of the member, and would not be up to a length of the member of about 50 cm.

Methods

Activation

As the properties which are relevant for the liquid handling ability of a liquid transport member according to the present invention are considered at the time of liquid transport, and as some of the materials or designs might have properties which differ from these, for example to ease transport or other handling between manufacturing of the member and its intended use, such members should also be activated before they are submitted to a test.

The term "activation" means, that the member is put into the in use condition, such as by establishing a liquid communication along a flow path, or such as by initiating a driving pressure differential, and this can be achieved by mechanical activation simulating the pre-use activation of a user (such as the removal of a constraining means such as a clamp, or a strip of a release paper such as with an adhesive, or removal of a package seal, thereby allowing mechanical expansion optionally with creation of a vacuum within the member).

Activation can further be achieved by another stimulus transmitted ton the activation means, such as pH or temperature change, by radiation or the like. Activation can also be achieved by interaction with liquids, such as having certain solubility properties, or changing concentrations, or are carrying activation ingredients like enzymes. This can also be achieved by the transport liquid itself, and in these instances, the member should be immersed in testing liquid which should be representative for the transport liquid, optionally removing the air by means of a vacuum pump, and allowing equilibration for 30 minutes. Then, the member is removed from the liquid, a put on a coarse mesh (such as a 14 mesh sieve) to allow dripping off of excess liquid.

Closed System Test

The test provides a simple to execute tool to assess if a transport material or member satisfies the principles of the present invention. It should be noted, that it is not useful to exclude materials or members, i.e. if a material or members does not pass the Closed System Test, it may or may not be a liquid transport member according to the present invention.

First, the test specimen is activated as described herein above, whilst the weight is monitored, and thus weight of the dry system as well as of the initial liquid can be determined. If the specimen contains significant amounts of liquid already prior to the activation, the weight of the initial liquid can be determined by conventional methods, such as drying under gentle conditions.

Then, the test specimen is suspended or supported in a position such that the longest extension of the sample is essentially aligned with the gravity vector. For example, the sample can be supported by a support board or mesh arranged at an angle of close to 90° to the horizontal, or the sample can be suspended by straps or bands in a vertical position. Thereby, the open port region should be positioned below the membrane port region, and be immersed in the liquid of a reservoir. The test specimen can be conveniently affixed to a weighing device, so as to allow monitoring of the weight through out the procedure. Also the reservoir is placed on a scale.

Then, as a next step, the wall region is opened both in the part of the sample and just above the liquid level of the reservoir, i.e., if the sample has sharp corners, then at these corners, if the sample has a curved or rounded periphery, then at the top of the periphery. The size of the opening has to be such as to allow liquid passing through the lower opening and air passing through the upper opening which is sufficient to allow liquid flowing out without adding pressure or squeezing. Typically, an opening having an inscribed circular diameter of at least 2 mm is adequate.

The opening can be done by any suitable means, such as by using a pair of scissors, a clipping tongue, needle, a sharp knife or a scalpel and the like. If a slit is applied to the sample, it should be done such that the flanks of the slit can move away from each other, so as to create a two-dimensional opening. Alternatively, a cut can remove a part of the wall material thus creating an opening.

Care should be taken that no additional weight is added, or pressure or squeezing is exerted on the sample. Similarly, care should be take, that no liquid is removed by the opening means, unless this could be accurately considered when calculating the weight differences.

If the material or member is a liquid transport member according to the present invention, liquid will flow through the opening or through the open port into the reservoir.

The weights of the system and of the reservoir are monitored, preferably no later than 10 minutes after opening of the test specimen. Care should be taken, that no excessive evaporation takes place, if this would be the case, this can be determined by monitoring the weight loss of a sample without having it opened over the test time, and by then correcting the results accordingly.

If the weight loss of the test specimen is more than or equal to 3% on the basis of the liquid in the test specimen prior to the opening, then the tested material or member has passed this test, and is a liquid transport member according to the present invention.

If the dripping weight less than 3% of the initial total weight, then this test does not allow assessment whether the material is a liquid transport member according to the present invention or not.

Bubble Point Pressure (Port Region)

The following procedure applies when it is desired to asses the bubble point pressure of a membrane port region or of a material useful for port regions.

First, the port region respectively the port region material is connected with a funnel and a tube as described in example A-1. Thereby, the lower end of the tube is left open i.e. not covered by a port region material. The tube should be of sufficient length, i.e. up to 10 m length may be required.

In case the test material is very thin, or fragile, it can be appropriate to support it by a very open support structure (as e.g. a layer of open pore non-woven material) before connecting it with the funnel and the tube.

In case the test specimen is not of sufficient size, the funnel may be replaced by a smaller one (e.g. Catalog # 625 616 02 from Fisher Scientific in Nidderau).

If the test specimen is too large size, a representative piece can be cut out so as to fit the funnel.

The testing liquid can be the transported liquid, but for ease of comparison, the testing liquid should a solution 0.03% TRITON X-100, such as available from MERCK KGaA, Darmsatdt, Germany, under the catalog number 1.08603, in destined or deionized water, thus resulting in a surface tension of 33 mN/m, when measured according to the surface tension method as described further.

The device is filled with testing liquid by immersing it in a reservoir of sufficient size filled with the testing fluid and by removing the remaining air with a vacuum pump.

Whilst keeping the lower (open) end of the funnel within the liquid in the reservoir, the part of the funnel with the port region is taken out of the liquid. If appropriate—but not necessarily—the funnel with the port region material should remain horizontally aligned.

Whilst slowly continuing to raise the port material above the reservoir, the height is monitored, and it is carefully observed through the funnel or through the port material itself (optionally aided by appropriate lighting) if air bubbles start to enter through the material into the inner of the funnel. At this point, the height above the reservoir is registered to be the bubble point height.

From this height H the Bubble point pressure BPP is calculated as: BPP=τ·g·H with the liquid density τ, gravity constant g (g≈9.81 m/s$^2$).

In particular for bubble point pressures exceeding about 50 kPa, an alternative determination can be used, such as commonly used for assessing bubble point pressures for membranes used in filtration systems.

Therein, the membrane is separating two liquid filled chambers, when one is set under an increased gas pressure (such as an air pressure), and the point is registered when the first air bubbles "break through".

Surface Tension Test Method

The surface tension measurement is well known to the man skilled in the art, such as with a Tensiometer K10T from Krüss GmbH, Hamburg, Germany using the DuNouy ring method as described in the equipment instructions. After cleaning the glassware with iso-propanol and de-ionized water, it is dried at 105° C. The Platinum ring is heated over a Bunsen-burner until red heat. A first reference measurement is taken to check the accuracy of the tensiometer. A suitable number of test replicates is taken to ensure consistency of the data. The resulting surface tension of thet liquid as expressed in units of mN/m can be used to determine the adhesion tension values and surface energy parameter of the respective liquid/solid/gas systems. Destilled water will generally exhibit a surface tension value of 72 mN/m, a 0.03% Triton X-100 solution of 33 mN/m.

Liquid Transport Test

The following test can be applied to liquid transport members having defined inlet and outlet port regions with a certain transport path length Ho between inlet and outlet port regions. For members, where the respective port regions cannot be determined such as because they are made of one homogeneous material, these regions may be defined by considering the intended use thus defining the respective port regions.

Before executing the test, the liquid transport member should be activated if necessary, as described in the above.

The test specimen is placed in a vertical position over a liquid reservoir, the open port positioned below the membrane port, such as by being suspended from a holder, whereby the open port remains completely immersed in liquid in the reservoir. The membrane port is connected such as via a flexible tubing of 6 mm outer diameter to a vacuum pump—optionally with a separator flask connected between the sample and the pump—and sealed in an air tight way as described in the above bubble point pressure method for a liquid transport member. The vacuum suction pressure differential can be monitored and adjusted.

The lowermost point of the membrane port is adjusted to be at a height $H_0$ above the liquid level in the reservoir.

The pressure differential is slowly increased to a pressure $P_0$=0.9 kPa+τg $H_0$ with the liquid density τ, and gravitational constant g (g≈9.81 m/s^2).

After reaching this pressure differential, the decrease of the weight of the liquid in the reservoir is monitored, preferably by positioning the reservoir on a scale measuring the weight of the reservoir, and connecting the scale to a computing equipment. After an initial unsteady decrease (typically taking not more than about one minute), the weight decrease in the reservoir will become constant (i.e. showing a straight line in a graphical data presentation). This constant weight decrease over time is the flow rate (in g/s) of the liquid transport member at suction of 0.9 kPa and a height $H_0$.

The corresponding flux rate of the liquid transport member at 0.9 kPa suction and a height $H_0$ is calculated from the flow rate by dividing the flow rate with the average cross section of the liquid transport member along a flow path, expressed in g/s/cm$^2$.

Care should be take, that the reservoir is large enough so that the fluid level in the reservoir does not change by more than 1 mm.

In addition, the effective permeability of the liquid transport member can be calculated by dividing the flux rate by the average length along a flow path and the driving pressure difference (0.9 kPa).

Liquid Permeability Test

Generally, the test should be carried out with a suitable test fluid representing the transport fluid. For example, when the application is in the context of absorbent disposable articles, Jayco SynUrine ss available from Jayco Pharmaceuticals Company of Camp Hill, Pa. has been found to be suitable. The formula for the synthetic urine is: 2.0 g/: of KCl; 2.0 g/l of Na2SO4; 0.85 g/l of (NH4)O4; 0.15 g/l (NH4)O4; 0.19 g/l of CaCl2; ad 0.23 g/l of MgCl2. All of the chemicals are of reagent grade. The pH of the synthetic Urine is in the range of 6.0 to 6.4. Also for such applications, it has been found useful to carry out the tests under controlled laboratory conditions of about 23+/−2° C. and at 50+/−10% relative humidity. Test specimen are stored under these conditions for at least 24 hours before testing, and—if applicable—activated as described in the above.

The present Permeability Test provides a measure for permeability for two special conditions: Either the permeability can be measured for a wide range of porous materials (such as non-wovens made of synthetic fibres, or cellulosic structures) at 100% saturation, or for materials, which reach different degrees of saturation with a proportional change in caliper without being filled with air (respectively the outside vapour phase), such as the collapsible polymeric foams, for which the permeability at varying degrees of saturation can readily be measured at various thicknesses.

In particular for polymeric foam materials, such as disclosed in U.S. Pat. No. 5,563,179 or U.S. Pat. No. 5,387,207 it has been found useful to operate the test at an elevated temperature of 31° C., so as to better simulate in-use conditions for absorbent articles.

In principle, this tests is based on Darcy's law, according to which the volumetric flow rate of a liquid through any porous medium is proportional to the pressure gradient, with the proportionality constant related to permeability.

$$Q/A = (k/\eta)*(\Delta P/L)$$

where:

Q=Volumetric Flow Rate [cm$^3$/s];

A=Cross Sectional Area [cm$^2$];

k=Permeability (cm$^2$) (with 1 Darcy corresponding to 9.869*10$^{-13}$ m$^2$);

η=Viscosity (Poise) [Pa*s];

ΔP/L=Pressure Gradient [Pa/m];

L=caliper of sample [cm].

Hence, permeability can be calculated—for a fixed or given sample cross-sectional area and test liquid viscosity—by measurement of pressure drop and the volumetric flow rate through the sample:

$$k = (Q/A)*(L/\Delta P)*\eta$$

The test can be executed in two modifications, the first referring to the transplanar permeability (i.e. the direction of flow is essentially along the thickness dimension of the material), the second being the in-plane permeability (i.e. the direction of flow being in the x-y-direction of the material).

Figure 9:
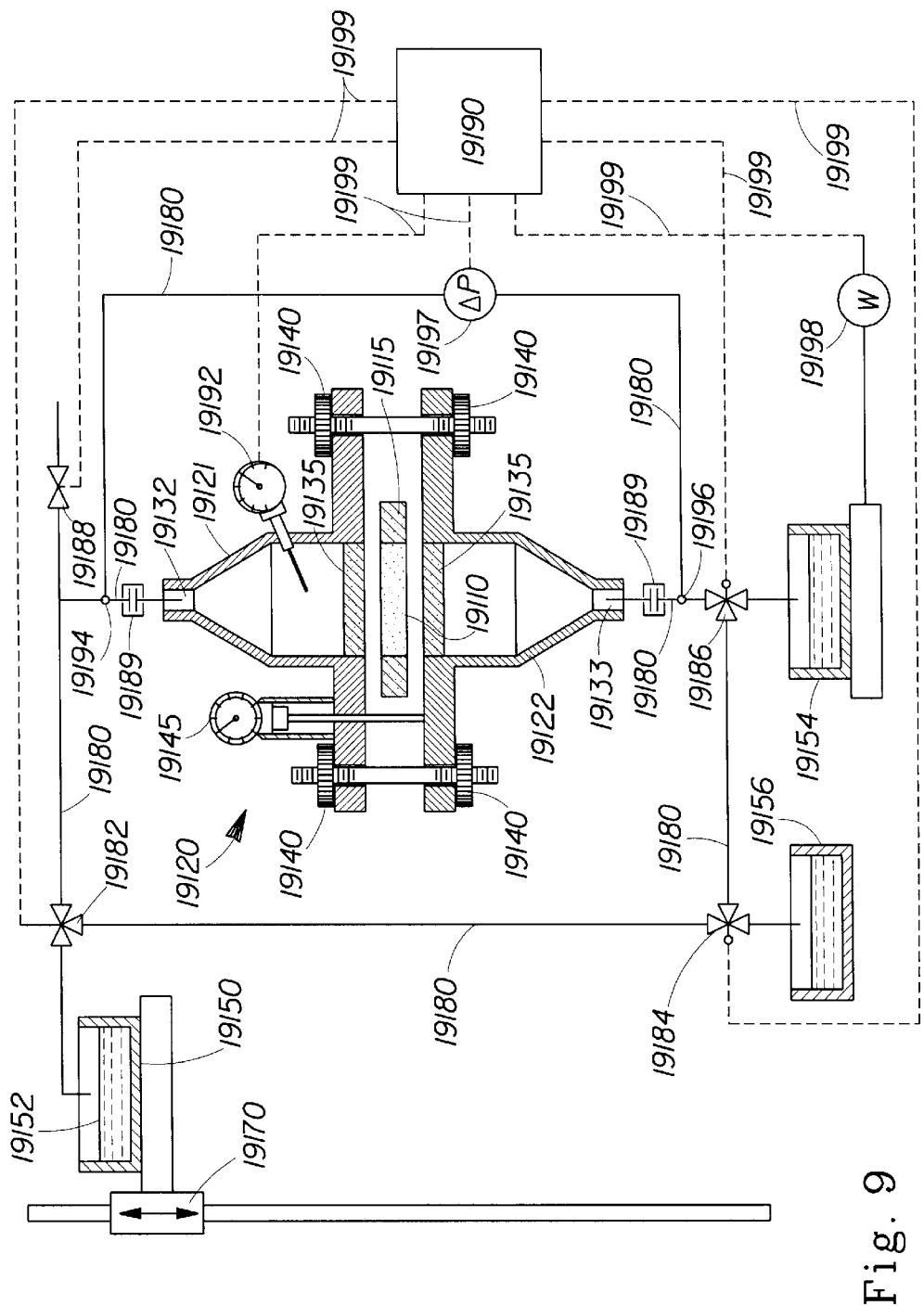
FIGS. 9 and 10A, B: Liquid permeability test.

The test set-up for the transplanar permeability test can be seen in FIG. 9 which is a schematic diagram of the overall equipment and—as an insert diagram—a partly exploded cross-sectional, not to scale view of the sample cell.

The test set-up comprises a generally circular or cylindrical sample cell (19120), having an upper (19121) and lower (19122) part. The distance of these parts can be measured and hence adjusted by means of each three circumferentially arranged caliper gauges (19145) and adjustment screws (19140). Further, the equipment comprises several fluid reservoirs (19150, 19154, 19156) including a height adjustment (19170) for the inlet reservoir (19150) as well as tubings (19180), quick release fittings (19189) for connecting the sample cell with the rest of the equipment, further valves (19182, 19184, 19186, 19188). The differential pressure transducer (19197) is connected via tubing (19180) to the upper pressure detection point (19194) and to the lower pressure detection point (19196). A Computer device (19190) for control of valves is further connected via connections (19199) to differential pressure transducer (19197), temperature probe (19192), and weight scale load cell (19198).

The circular sample (19110) having a diameter of 1 in (about 2.54 cm) is placed in between two porous screens (19135) inside the sample cell (19120), which is made of two 1 in (2.54 cm) inner diameter cylindrical pieces (19121, 19122) attached via the inlet connection (19132) to the inlet reservoir (19150) and via the outlet connection (19133) to the outlet reservoir (19154) by flexible tubing (19180), such as tygon tubing. Closed cell foam gaskets (19115) provide leakage protection around the sides of the sample. The test sample (19110) is compressed to the caliper corresponding to the desired wet compression, which is set to 0.2 psi (about 1.4 kPa) unless otherwise mentioned. Liquid is allowed to flow through the sample (19110) to achieve steady state flow. Once steady state flow through the sample (19110) has been established, volumetric flow rate and pressure drop are recorded as a function of time using a load cell (19198) and the differential pressure transducer (19197). The experiment can be performed at any pressure head up to 80 cm water (about 7.8 kPa), which can be adjusted by the height adjusting device (19170). From these measurements, the flow rate at different pressures for the sample can be determined.

The equipment is commercially available as a Permeameter such as supplied by Porous Materials, Inc, Ithaca, N.Y., US under the designation PMI Liquid Permeameter, such as further described in respective user manual of 2/97. This equipment includes two Stainless Steel Frits as porous screens (19135), also specified in said brochure. The equipment consists of the sample cell (19120), inlet reservoir (19150), outlet reservoir (19154), and waste reservoir (19156) and respective filling and emptying valves and connections, an electronic scale, and a computerized monitoring and valve control unit (19190).

The gasket material (19115) is a Closed Cell Neoprene Sponge SNC-1 (Soft), such as supplied by Netherland Rubber Company, Cincinnati, Ohio, US. A set of materials with varying thickness in steps of ¹⁄₁₆" (about 0.159 cm) should be available to cover the range from ¹⁄₁₆"½" (about 0.159 cm to about 1.27 cm) thickness.

Further a pressurized air supply is required, of at least 60 psi (4.1 bar), to operate the respective valves.

Test fluid is deionized water.

The test is then executed by the following steps:

1) Preparation of the Test Sample(s)

In a preparatory test, it is determined, if one or more layers of the test sample are required, wherein the test as outlined below is run at the lowest and highest pressure. The number of layers is then adjusted so as to maintain the flow rate during the test between 0.5 cm³/seconds at the lowest pressure drop and 15 cm³/second at the highest pressure drop. The flow rate for the sample should be less than the flow rate for the blank at the same pressure drop. If the sample flow rate exceeds that of the blank for a given pressure drop, more layers should be added to decrease the flow rate.

Sample size: Samples are cut to 1" (about 2.54 cm) diameter, by using an arch punch, such as supplied by McMaster-Carr Supply Company, Cleveland, Ohio, US. If samples have too little internal strength or integrity to maintain their structure during the required manipulation, a conventional low basis weight support means can be added, such as a PET scrim or net.

Thus, at least two samples (made of the required number of layers each, if necessary) are precut. Then, one of these is saturated in deionized water at the temperature the experiment is to be performed (70° F., (31° C.) unless otherwise noted).

The caliper of the wet sample is measured (if necessary after a stabilization time of 30 seconds) under the desired compression pressure for which the experiment will be run by using a conventional caliper gauge (such as supplied by AMES, Waltham, Mass., US) having a pressure foot diameter of 1 ⅛" (about 2.86 cm), exerting a pressure of 0.2 psi (about 1.4 kPa) on the sample (19110), unless otherwise desired.

An appropriate combination of gasket materials is chosen, such that the total thickness of the gasketing foam (19115) is between 150 and 200% of the thickness of the wet sample (note that a combination of varying thicknesses of gasket material may be needed to achieve the overall desired thickness). The gasket material (19115) is cut to a circular size of 3" in diameter, and a 1 inch (2.54 cm) hole is cut into the center by using the arch punch.

In case, that the sample dimensions change upon wetting, the sample should be cut such that the required diameter is taken in the wet stage. This can also be assessed in this preparatory test, with monitoring of the respective dimensions. If these change such that either a gap is formed, or the sample forms wrinkles which would prevent it from smoothly contacting the porous screens or frits, the cut diameter should be adjusted accordingly.

The test sample (19110) is placed inside the hole in the gasket foam (19115), and the composite is placed on top of the bottom half of the sample cell, ensuring that the sample is in flat, smooth contact with the screen (19135), and no gaps are formed at the sides.

The top of the test cell (19121) is laid flat on the lab bench (or another horizontal plane) and all three caliper gauges (19145) mounted thereon are zeroed.

The top of the test cell (19121) is then placed onto the bottom part (19122) such that the gasket material (19115) with the test sample (19110) lays in between the two parts. The top and bottom part are then tightened by the fixation screws (19140), such that the three caliper gauges are adjusted to the same value as measured for the wet sample under the respective pressure in the above.

2) To prepare the experiment, the program on the computerized unit (19190) is started and sample identification, respective pressure etc. are entered.

3) The test will be run on one sample (19110) for several pressure cycles, with the first pressure being the lowest pressure. The results of the individual pressure runs are put on different result files by the computerized unit (19190). Data are taken from each of these files for the calculations as described below. (A different sample should be used for any subsequent runs of the material.)

4) The inlet liquid reservoir (19150) is set to the required height and the test is started on the computerized unit (19190).

5) Then, the sample cell (19120) is positioned into the permeameter unit with Quick Disconnect fittings (19189).

6) The sample cell (19120) is filled by opening the vent valve (19188) and the bottom fill valves (19184, 19186). During this step, care must be taken to remove air bubbles from the system, which can be achieved by turning the sample cell vertically, forcing air bubbles—if present—to exit the permeameter through the drain.

Once the sample cell is filled up to the tygon tubing attached to the top of the chamber (19121), air bubbles are removed from this tubing into the waste reservoir (19156).

7) After having carefully removed air bubbles, the bottom fill valves (19184, 19186) are closed, and the top fill (19182) valve is opened, so as to fill the upper part, also carefully removing all air bubbles.

8) The fluid reservoir is filled with test fluid to the fill line (19152).

Then the flow is started through the sample by initiating the computerized unit (19190).

After the temperature in the sample chamber has reached the required value, the experiment is ready to begin.

Upon starting the experiment via the computerized unit (19190), the liquid outlet flow is automatically diverted from the waste reservoir (19156) to the outlet reservoir (19154), and pressure drop, and temperature are monitored as a function of time for several minutes.

Once the program has ended, the computerized unit provides the recorded data (in numeric and/or graphical form).

If desired, the same test sample can be used to measure the permeability at varying pressure heads, with thereby increasing the pressure from run to run.

The equipment should be cleaned every two weeks, and calibrated at least once per week, especially the frits, the load cell, the thermocouple and the pressure transducer, thereby following the instructions of the equipment supplier.

The differential pressure is recorded via the differential pressure transducer connected to the pressure probes measurement points (19194,19196) in the top and bottom part of the sample cell. Since there may be other flow resistances within the chamber adding to the pressure that is recorded, each experiment must be corrected by a blank run. A blank run should be done at 10, 20, 30, 40, 50, 60, 70, 80 cm requested pressure, each day. The permeameter will output a Mean Test Pressure for each experiment and also an average flow rate.

For each pressure that the sample has been tested at, the flow rate is recorded as Blank Corrected Pressure by the computerized unit (19190), which is further correcting the Mean Test Pressure (Actual Pressure) at each height recorded pressure differentials to result in the Corrected Pressure. This Corrected Pressure is the DP that should be used in the permeability equation below.

Permeability can then be calculated at each requested pressure and all permeabilities should be averaged to determine the k for the material being tested.

Three measurements should be taken for each sample at each head and the results averaged and the standard deviation calculated. However, the same sample should be used, permeability measured at each head, and then a new sample should be used to do the second and third replicates.

Figure 10A:
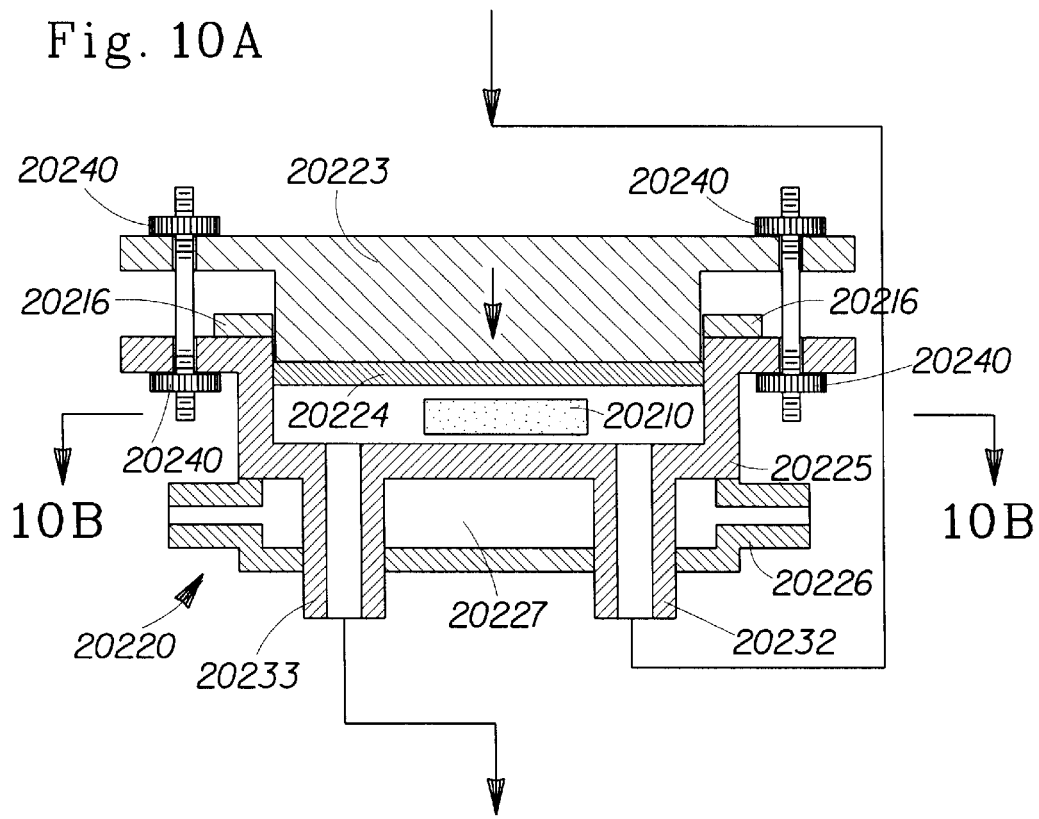
Figure 10B:
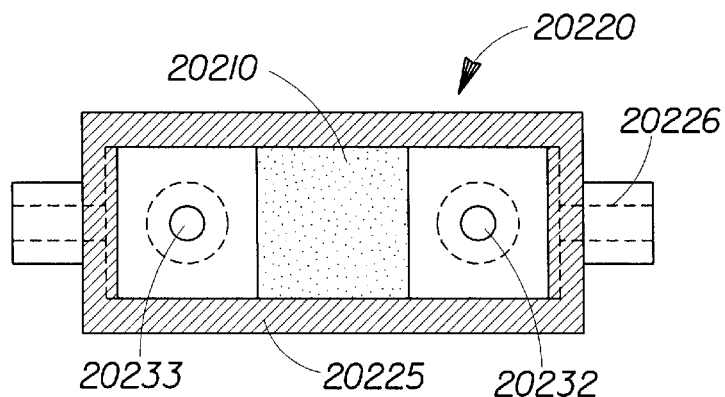

The measuring of the in-plane permeability under the same conditions as the above described transplanar permeability, can be achieved by modifying the above equipment such as schematically depicted in FIGS. 10A and 10B showing the partly exploded, not to scale view of the sample cell only. Equivalent elements are denoted equivalently, such that the sample cell of FIG. 10 is denoted (20210), correlating to the numeral (19110) of FIG. 9, and so on. Thus, the transplanar sample cell (19120) of FIG. 9 is replaced by the in-plane simplified cell (20220), which is designed so that liquid can flow only in one direction (either machine direction or cross direction depending on how the sample is placed in the cell). Care should be taken to minimize channeling of liquid along the walls (wall effects), since this can erroneously give high permeability reading. The test procedure is then executed quite analogous to the transplanar test.

The sample cell (20220) is designed to be positioned into the equipment essentially as described for the sample cell (20120) in the above transplanar test, except that the filling tube is directed to the inlet connection (20232) the bottom of the cell (20220). FIG. 10A shows a partly exploded view of the sample cell, and FIG. 10B a cross-sectional view through the sample level.

The test cell (20220) is made up of two pieces: a bottom piece (20225) which is like a rectangular box with flanges, and a top piece (20223) that fits inside the bottom piece (20225) and has flanges as well. The test sample is cut to the size of 2" in×2" in (about 5.1 cm by 5.1 cm) and is placed into the bottom piece. The top piece (20223) of the sample chamber is then placed into the bottom piece (20225) and sits on the test sample (20210). An incompressible neoprene rubber seal (20224) is attached to the upper piece (20223) to provide tight sealing. The test liquid flows from the inlet reservoir to the sample space via Tygon tubing and the inlet connection (20232) further through the outlet connection (20233) to the outlet reservoir. As in this test execution the temperature control of the fluid passing through the sample cell can be insufficient due to lower flow rates, the sample is kept at the desired test temperature by the heating device (20226), whereby thermostated water is pumped through the heating chamber (20227). The gap in the test cell is set at the caliper corresponding to the desired wet compression, normally 0.2 psi (about 1.4 kPa). Shims (20216) ranging in size from 0.1 mm to 20.0 mm are used to set the correct caliper, optionally using combinations of several shims.

At the start of the experiment, the test cell (20220) is rotated 90° (sample is vertical) and the test liquid allowed to enter slowly from the bottom. This is necessary to ensure that all the air is driven out from the sample and the inlet/outlet connections (20232/20233). Next, the test cell (20220) is rotated back to its original position so as to make the sample (20210) horizontal. The subsequent procedure is the same as that described earlier for transplanar permeability, i.e. the inlet reservoir is placed at the desired height, the flow is allowed to equilibrate, and flow rate and pressure drop are measured. Permeability is calculated using Darcy's law. This procedure is repeated for higher pressures as well.

For samples that have very low permeability, it may be necessary to increase the driving pressure, such as by extending the height or by applying additional air pressure on the reservoir in order to get a measurable flow rate. In plane permeability can be measured independently in the machine and cross directions, depending on how the sample is placed in the test cell.

Determination of Pore Size

Optical determination of pore size is especially used for thin layers of porous system by using standard image analysis procedures know to the skilled artisan.

The principle of the method consists of the following steps: 1) A thin layer of the sample material is prepared by either slicing a thick sample into thinner sheets or if the sample itself is thin by using it directly. The term "thin" refers to achieving a sample caliper low enough to allow a clear cross-section image under the microscope. Typical sample calipers are below 200 μm. 2) A microscopic image is obtained via a video microscope using the appropriate magnification. Best results are obtained if about 10 to 100 pores are visible on said image. The image is then digitized by a standard image analysis package such as OPTIMAS by BioScan Corp. which runs under Windows 95 on a typical IBM compatible PC. Frame grabber of sufficient pixel resolution (preferred at least 1024×1024 pixels) should be used to obtain good results. 3) The image is converted to a binary image using an appropriate threshold level such that the pores visable on the image are marked as object areas in white and the rest remains black. Automatic threshold setting procedures such as available under OPTIMAS can be used. 4) The areas of the individual pores (objects) are determined. OPTIMAS offers fully automatic determination of the areas. 5) The equivalent radius for each pore is determined by a circle that would have the same area as the pore. If A is the area of the pore, then the equivalent radius is given by $r=(A/\pi)^{1/2}$. The average pore size can then be determined from the pore size distribution using standard statistical rules. For materials that have a not very uniform pore size it is recommended to use at least 3 samples for the determination. Alternative equipments useful for determining pores sizes are commercially available Porosimeter or Permeater Tester, such as a Permeameter supplied by Porous Materials, Inc, Ithaca, N.Y., US under the designation PMI Liquid Permeameter model no. CFP-1200AEXI, such as further described in respective user manual of 2/97.

Teabag Centrifuge Capacity Test (TCC Test)

Whilst the TCC test has been developed specifically for superabsorbent materials, it can readily be applied to other absorbent materials.

The Teabag Centrifuge Capacity test measures the Teabag Centrifuge Capacity values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two liters of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Düsseldorf, Germany. The pouch is heat sealable with a standard kitchen plastic bag sealing device (e.g. VACUPACK2 PLUS from Krups, Germany).

The teabag is opened by carefully cutting it partially, and is then weighed. About 0.200 g of the sample of the absorbent material, accurately weighed to +/−0.005 g, is placed in the teabag. The teabag is then closed with a heat sealer. This is called the sample teabag. An empty teabag is sealed and used as a blank.

The sample teabag and the blank teabag are then laid on the surface of the saline solution, and submerged for about 5 seconds using a spatula to allow complete wetting (the teabags will float on the surface of the saline solution but are then completely wetted). The timer is started immediately. After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilised at 1,400 rpm the timer is started. After 3 minutes, the centrifuge is stopped.

The sample teabag and the blank teabag are removed and weighed separately.

The Teabag Centrifuge Capacity (TCC) for the sample of absorbent material is calculated as follows:

TCC=[(sample teabag weight after centrifuging)−(blank teabag weight after centrifuging)−(dry absorbent material weight)] ÷(dry absorbent material weight).

What is claimed is:

1. Liquid transport member comprising at least one bulk region and a wall region that completely circumscribes said bulk region, said wall region further comprising at least one membrane port region and at least one open port region, characterized in that said bulk region has an average fluid permeability $k_b$ which is higher than the average fluid permeability $k_p$ of the membrane port region and said membrane port region is effective for transporting a selected liquid, while substantially preventing entry of gas into the transport member in use.

2. Liquid transport member according to claim 1, wherein said bulk region has a fluid permeability of at least $10^{-11} m^2$.

3. Liquid transport member according to claim 1, wherein said membrane port region has a fluid permeability of at least $6*10^{-20} m^2$.

4. Liquid transport member according to claim 1, wherein said membrane port region has a ratio of fluid permeability to thickness in a direction of liquid transport, $k_p/d_p$ of at least $3*10^{-15}$ m.

5. Liquid transport member according to claim 1, wherein said membrane port region is arranged above said open port region during its intended use.

6. Liquid transport member according to claim 1, wherein said open port region is an opening having an inner circular diameter of less than the corresponding diameter $d_b$ of a gas bubble formed in the liquid within the bulk region.

7. Liquid transport member according to claim 1, wherein said open port region is an opening having a inner circular diameter of less than 6 mm.

8. Liquid transport member according to claim 1, wherein the ratio of permeability of the bulk region to the permeability of the membrane port region is at least 10.

9. Liquid transport member according to claim 1, wherein said membrane port region has a bubble point pressure as measured with a liquid having a surface tension value of 72 mN/m of at least 1 kPa.

10. Liquid transport member according to claim 1, wherein said membrane port region has a bubble point pressure as measured with a liquid having a surface tension value of 33 mN/m of at least 0.67 kPa.

11. Liquid transport member according to claim 1, wherein said bulk region has a larger average pore size than said membrane port region, preferably such that the ratio of average pore size of the bulk region and the average pore size of the membrane port region is at least 10.

12. Liquid transport member according to claim 1, wherein said bulk region has an average pore size of at least 200 μm.

13. Liquid transport member according to claim 1, wherein said bulk region has a porosity of at least 50%.

14. Liquid transport member according to claim 1, wherein said bulk region is a void circumscribed by a wall region.

15. Liquid transport member according to claim 1, wherein said membrane port region has a porosity of at least 10%.

16. Liquid transport member according to claim 1, wherein said membrane port region has an average pore size of no more than 100 μm.

17. Liquid transport member according to claim 1, wherein said membrane port region has a pore size of at least 1 μm.

18. Liquid transport member according to claim 1, wherein said membrane port region has an average thickness of no more than 100 μm.

19. Liquid transport member according to claim 1, wherein said bulk region and said wall region have a volume ratio of at least 10.

20. Liquid transport member according to claim 1, wherein said membrane port region is hydrophilic.

21. Liquid transport member according to claim 20 wherein the membrane port region does not substantially decrease the liquid surface tension of the liquid that is to be transported.

22. Liquid transport member according to claim 1, wherein said membrane port region is oleophilic.

23. Liquid transport member according to claim 1 which has a sheet-like shape, or has a cylindrical like shape.

24. Liquid transport member according to claim 1, wherein the cross-section area of the member along a direction of liquid transport is not constant.

25. Liquid transport member according to claim 1, wherein the membrane port region has a larger area than the average cross-section of the member along a direction of liquid transport.

26. Liquid transport member according to claim 1, comprising a material which is expandable upon liquid contact and collapsible upon liquid removal.

27. Liquid transport member according to claim 1, wherein said bulk region comprises a material selected from fibers, particulates, foams, spirals, films, corrugated sheets, or tubes.

28. Liquid transport member according to claim 1, wherein said wall region comprises a material selected from fibers, particulates, foams, spirals, films, corrugated sheets, tubes, woven webs, woven fiber meshes, apertured films, or monolithic films.

29. Liquid transport member according to claims 27 or 28, wherein said bulk region or wall region comprises an open cell reticulated foam selected from cellulose sponge, polyurethane foam, and HIPE foams.

30. Liquid transport member according to claims 27 or 28, wherein said bulk region or wall region comprises fibers made of polyolefins, polyesters, polyamids, polyethers, polyacrylics, polyurethanes, metal, glass, cellulose, and cellulose derivatives.

31. Liquid transport member according to claim 1 wherein the member is made by a porous bulk region that is wrapped by a separate wall region.

32. Liquid transport member according to claim 1 comprising water soluble materials.

33. Liquid transport member according to claim 32, wherein at least one of the port regions comprises a water soluble material.

34. Liquid transport member according to claim 1 adapted for transport of water-based liquids or of viscoelastic liquids.

35. Liquid transport member according to claim 1 adapted for transport of oil, grease, or other non-water based liquids.

36. Liquid transport member according to claim 35 adapted for selective transport of oil or grease, but not water based liquids.

37. Liquid transport member according to claim 1, wherein at least one member property or parameter is established prior to or at the liquid handling by activation by contact with the liquid, pH, temperature, enzymes, chemical reaction, salt concentration or mechanical activation.

38. A liquid transport system comprising a liquid transport member according to claim 1 and a source of liquid and a sink of liquid that are outside the liquid transport member.

39. A liquid transport system according to claim 38, wherein the open port region is immersed in liquid of said sink or source.

40. A liquid transport system according to claim 38, having an absorption capacity of at least 5 g/g when submitted to the Demand Absorbency Test.

41. Liquid transport system according to claim 38, comprising a sink material that has an absorption capacity of at least 10 g/g on the basis of the weight of the sink material, when submitted to the Teabag Centrifuge Capacity Test.

42. Liquid transport system according to claim 38, comprising superabsorbent material or open celled foam of the High Internal Phase Emulsion (HIPE) type.

43. Liquid transport system according to claim 38, further comprising a mechanical liquid pump.

44. An article comprising a liquid transport member according to claim 1.

45. An article according to claim 44 which is a grease absorber.

46. An article according to claim 44 which is a water transport member.

* * * * *

UNITED STATES PATENT AND TRADEMARK OFFICE
CERTIFICATE OF CORRECTION

PATENT NO. : 6,579,457 B1
DATED : June 17, 2003
INVENTOR(S) : Bruno J. Ehrnsperger et al.

It is certified that error appears in the above-identified patent and that said Letters Patent is hereby corrected as shown below:

Columns 23-24,
Lines 49-20, delete "membrane" thru "appropriate".

Column 27,
Line 54, delete "gass" and insert -- gas --.

Column 31,
Line 59, delete "Bamant" and insert -- Barnant --.

Column 32,
Line 10, delete "Fedemfabrik" and insert -- Federnfabrik --.

Column 34,
Line 53, delete "destined" and insert -- distilled --.

Signed and Sealed this

Fourteenth Day of February, 2006

JON W. DUDAS
*Director of the United States Patent and Trademark Office*